United States Patent
Liu et al.

(10) Patent No.: US 10,351,743 B2
(45) Date of Patent: Jul. 16, 2019

(54) PROTEIN-BASED ADHESIVES

(71) Applicants: Julie C. Liu, West Lafayette, IN (US); Jonathan James Wilker, Lafayette, IN (US); Mary Jane Brennan, Lafayette, IN (US); Charng-yu Lin, West Lafayette, IN (US)

(72) Inventors: Julie C. Liu, West Lafayette, IN (US); Jonathan James Wilker, Lafayette, IN (US); Mary Jane Brennan, Lafayette, IN (US); Charng-yu Lin, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 91 days.

(21) Appl. No.: 15/230,762

(22) Filed: Aug. 8, 2016

(65) Prior Publication Data

US 2017/0015885 A1    Jan. 19, 2017

Related U.S. Application Data

(63) Continuation-in-part of application No. 15/212,152, filed on Jul. 15, 2016.

(60) Provisional application No. 62/193,069, filed on Jul. 15, 2015.

(51) Int. Cl.
*C07K 7/06*  (2006.01)
*C07K 14/78* (2006.01)
*C09J 189/00* (2006.01)

(52) U.S. Cl.
CPC .............. *C09J 189/00* (2013.01); *C07K 7/06* (2013.01); *C07K 14/78* (2013.01); *C07K 2319/00* (2013.01)

(58) Field of Classification Search
None
See application file for complete search history.

(56) References Cited

PUBLICATIONS

Kim et al. ("Self-Assembly of Thermally Responsive Amphiphilic Diblock Copolypeptides into Spherical Micellar Nanoparticles," Angew. Chem. Int. Ed. 2010, 49, 4257-4260) (Year: 2010).*

* cited by examiner

*Primary Examiner* — Christina Bradley
(74) *Attorney, Agent, or Firm* — Reichel Stohry LLP; Natalie J. Dean; Mark C. Reichel

(57) ABSTRACT

Protein-based adhesives. In one embodiment of the present disclosure, an elastin-like polypeptide has a sequence LDGTL-(PGX$_1$GVPGKGVPGX$_2$GVPGX$_1$GVPGX$_3$GVPGX$_2$GV)$_n$-PVADRGMRLE, wherein each X$_1$ is selected from the group consisting of tyrosine (Y), dihydroxyphenylalanine (DOPA), and 3,4,5-trihydroxyphenylalanine (TOPA), wherein each X$_2$ is selected from the group consisting of valine (V), Y, DOPA, and TOPA, wherein each X$_3$ is selected from the group consisting of glutamic acid (E) and lysine (K), and wherein n is at or between 6 and 10 or higher or lower.

16 Claims, 18 Drawing Sheets

Specification includes a Sequence Listing.

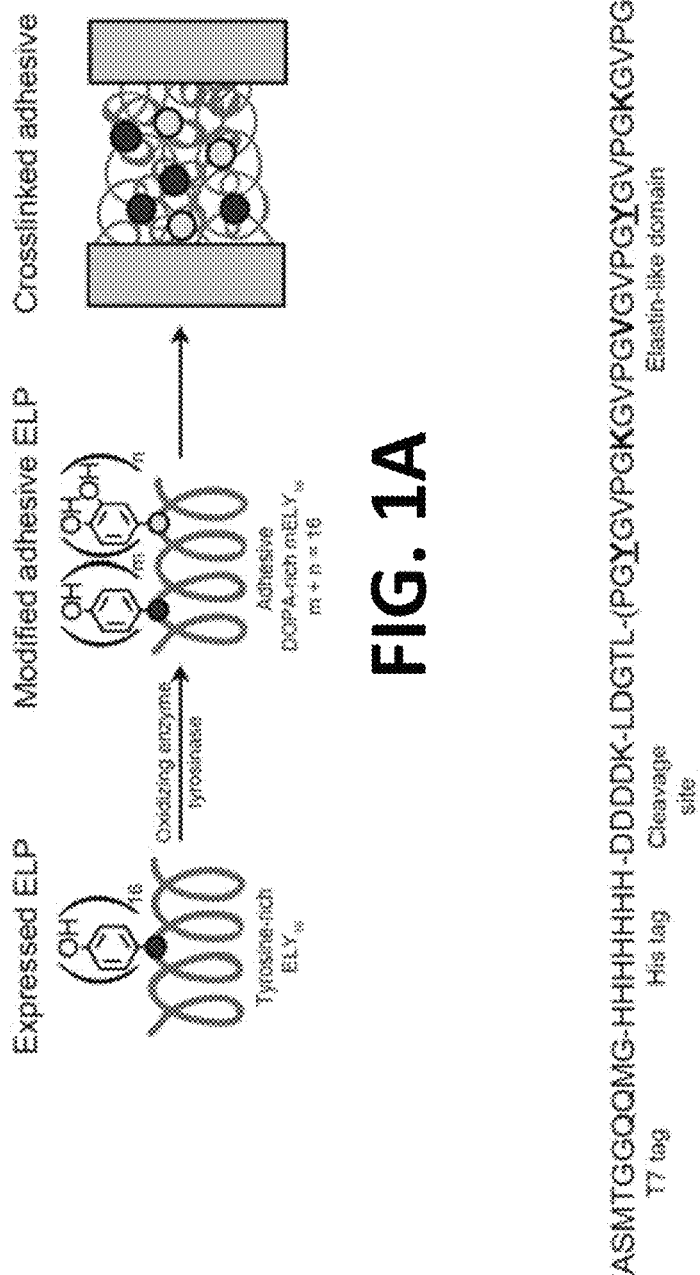

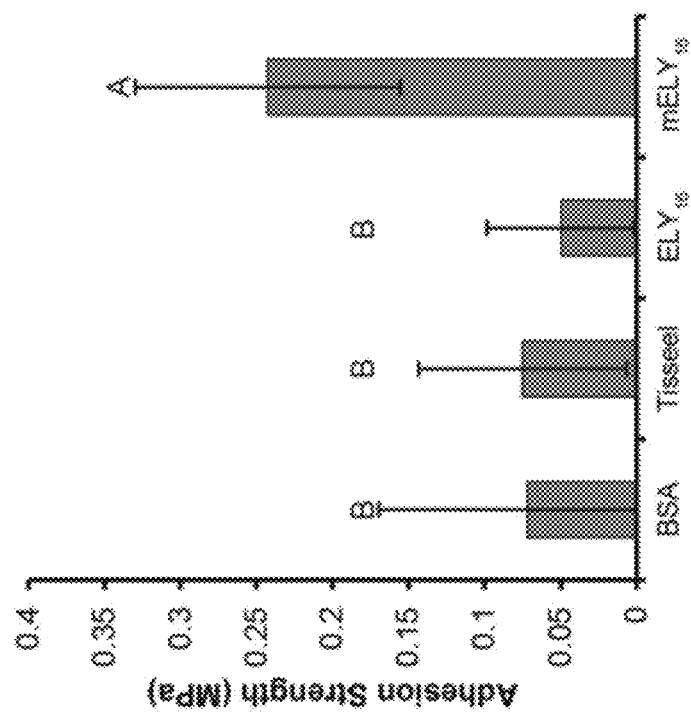
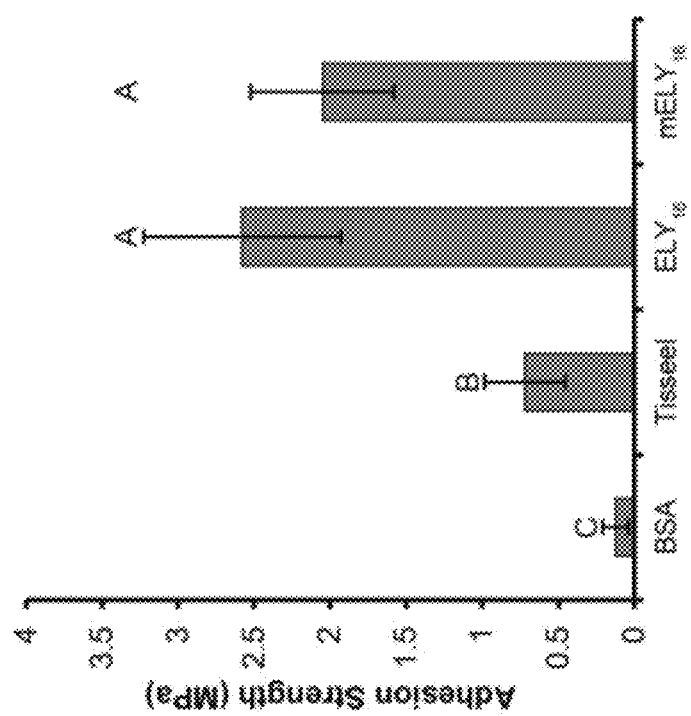
FIG. 4A
FIG. 4B

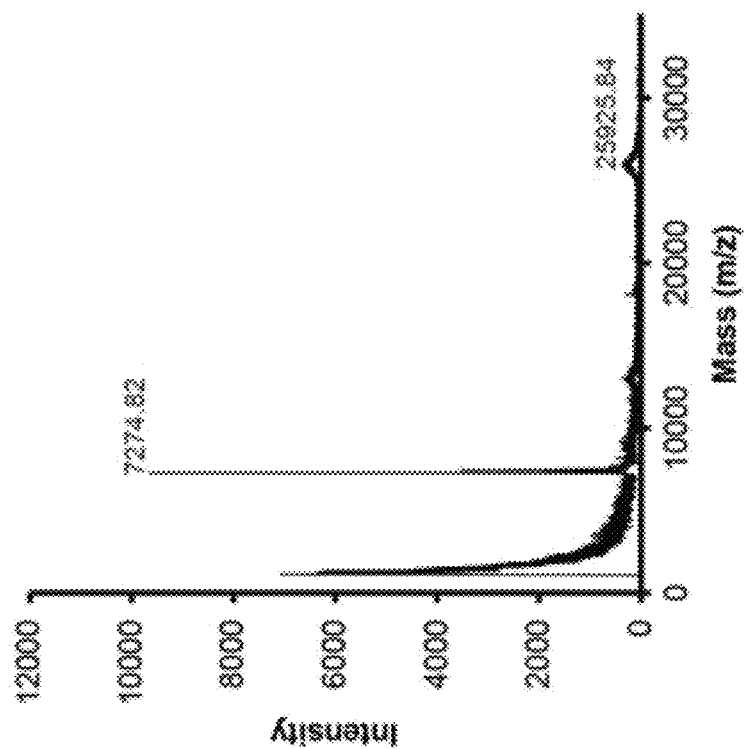
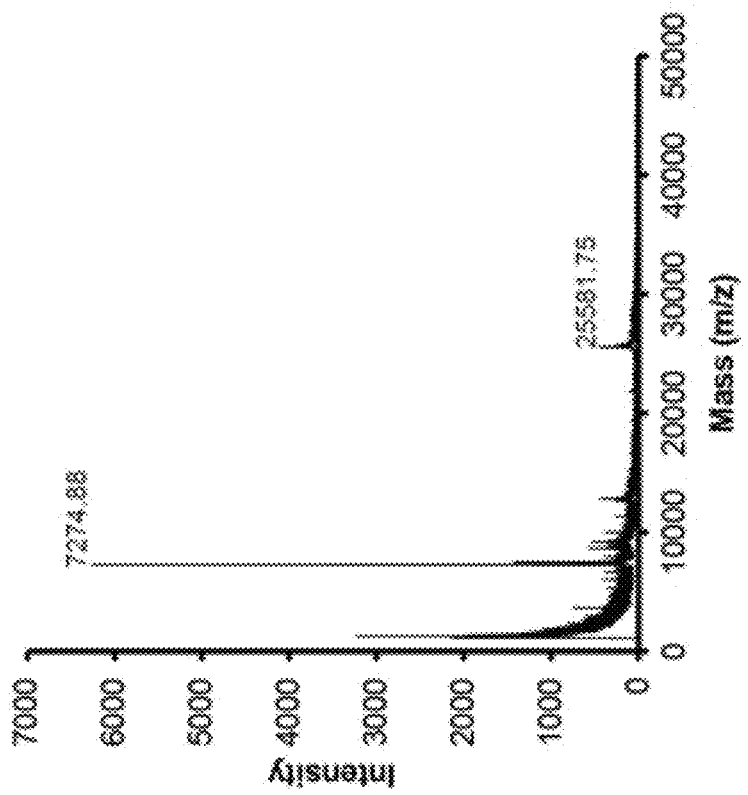
FIG. 6B
FIG. 6A

| Amino Acid | Expected mol% | ELY$_{16}$ Observed mol% | mELY$_{16}$ Observed mol% |
| --- | --- | --- | --- |
| ASX | 2.19 | 2.42 | 2.08 |
| THR | 0.73 | 0.87 | 0.96 |
| SER | 0.36 | 0.52 | 0.40 |
| GLX | 1.09 | 1.55 | 0.78 |
| PRO | 17.88 | 17.15 | 16.42 |
| GLY | 36.86 | 36.13 | 37.09 |
| ALA | 0.73 | 1.5 | 0.77 |
| VAL | 23.72 | 22.69 | 25.53 |
| ILE | 0.00 | 0.18 | 0.00 |
| LEU | 1.09 | 1.20 | 1.11 |
| PHE | 0.00 | 0.12 | 0.23 |
| HIS | 2.55 | 2.26 | 2.57 |
| LYS | 6.20 | 6.94 | 6.48 |
| ARG | 0.73 | 0.81 | 0.71 |
| TYR | 5.84 | 5.66 | 0.68 |
| DOPA | N/A | 0.00 | 4.19 |

FIG. 7

SEQUENCE LISTING

```
<160> NUMBER OF SEQ ID NOS: 13

<210> SEQ ID NO 1
<211> LENGTH: 30
<212> TYPE: PRT
<213> ORGANISM: Artificial Sequence
<220> FEATURE:
<223> OTHER INFORMATION: Sequence per se is derived from human thought
<220> FEATURE:
<221> NAME/KEY: MISC_FEATURE
<222> LOCATION: (3)..(3)
<223> OTHER INFORMATION: Xaa at position 3 be Y, dihydroxyphenylalanine
      (DOPA), or 3, 4, 5-trihydroxyphenylalanine (TOPA)
<220> FEATURE:
<221> NAME/KEY: MISC_FEATURE
<222> LOCATION: (13)..(13)
<223> OTHER INFORMATION: Xaa at position 13 may be V, Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (18)..(18)
<223> OTHER INFORMATION: Xaa at position 18 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (23)..(23)
<223> OTHER INFORMATION: Xaa at position 23 may be E or K
<220> FEATURE:
<221> NAME/KEY: MISC_FEATURE
<222> LOCATION: (28)..(28)
<223> OTHER INFORMATION: Xaa at position 28 may be V, Y,
      dihydroxyphenylalanine (DOPA), or 3, 4, 5-trihydroxyphenylalanine
      (TOPA)

<400> SEQUENCE: 1

Pro Gly Xaa Gly Val Pro Gly Lys Gly Val Pro Gly Xaa Gly Val Pro
1               5                   10                  15
```

```
Gly Xaa Gly Val Pro Gly Xaa Gly Val Pro Gly Xaa Gly Val
            20                  25                  30

<210> SEQ ID NO 2
<211> LENGTH: 45
<212> TYPE: PRT
<213> ORGANISM: Artificial Sequence
<220> FEATURE:
<223> OTHER INFORMATION: Sequence is SEQ ID NO. 1 preceded by SEQ ID NO.
      10 and followed by SEQ ID NO. 12
<220> FEATURE:
<221> NAME/KEY: REPEAT
<222> LOCATION: (6)..(35)
<223> OTHER INFORMATION: The series of residues from positions 6-35 may
      be repeated 6, 7, 8, 9, 10, or n times
<220> FEATURE:
<221> NAME/KEY: MISC_FEATURE
<222> LOCATION: (8)..(8)
<223> OTHER INFORMATION: Xaa at position 8 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (18)..(18)
<223> OTHER INFORMATION: Xaa at position 18 may be V, Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (23)..(23)
<223> OTHER INFORMATION: Xaa at position 23 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (28)..(28)
<223> OTHER INFORMATION: Xaa at position 28 may be E or K
<220> FEATURE:
<221> NAME/KEY: MISC_FEATURE
<222> LOCATION: (33)..(33)
<223> OTHER INFORMATION: Xaa at position 33 may be V, Y,
      dihydroxyphenylalanine (DOPA), or 3, 4, 5-trihydroxyphenylalanine
      (TOPA)

<400> SEQUENCE: 2

Leu Asp Gly Thr Leu Pro Gly Xaa Gly Val Pro Gly Lys Gly Val Pro
1               5                   10                  15

Gly Xaa Gly Val Pro Gly Xaa Gly Val Pro Gly Xaa Gly Val Pro Gly
            20                  25                  30

Xaa Gly Val Pro Val Ala Asp Arg Gly Met Arg Leu Glu
            35                  40                  45

<210> SEQ ID NO 3
<211> LENGTH: 51
<212> TYPE: PRT
<213> ORGANISM: Artificial Sequence
<220> FEATURE:
<223> OTHER INFORMATION: Sequence is SEQ ID NO. 1 preceded by SEQ ID NO.
      11 and followed by SEQ ID NO. 12
<220> FEATURE:
<221> NAME/KEY: REPEAT
<222> LOCATION: (12)..(41)
<223> OTHER INFORMATION: The series of residues from positions 12-41 may
      be repeated 6, 7, 8, 9, 10, or n times
<220> FEATURE:
<221> NAME/KEY: MISC_FEATURE
<222> LOCATION: (14)..(14)
<223> OTHER INFORMATION: Xaa at position 14 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (24)..(24)
```

```
<223> OTHER INFORMATION: Xaa at position 24 may be V, Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (29)..(29)
<223> OTHER INFORMATION: Xaa at posotion 29 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (34)..(34)
<223> OTHER INFORMATION: Xaa at position 34 may be E or K
<220> FEATURE:
<221> NAME/KEY: MISC_FEATURE
<222> LOCATION: (39)..(39)
<223> OTHER INFORMATION: Xaa at position 39 may be V, Y,
      dihydroxyphenylalanine (DOPA), or 3, 4, 5-trihydroxyphenylalanine
      (TOPA)

<400> SEQUENCE: 3

Met Ser Lys Gly Pro Gly Val Asp Gly Thr Leu Pro Gly Xaa Gly Val
1               5                   10                  15

Pro Gly Lys Gly Val Pro Gly Xaa Gly Val Pro Gly Xaa Gly Val Pro
            20                  25                  30

Gly Xaa Gly Val Pro Gly Xaa Gly Val Pro Val Ala Asp Arg Gly Met
        35                  40                  45

Arg Leu Glu
    50

<210> SEQ ID NO 4
<211> LENGTH: 57
<212> TYPE: PRT
<213> ORGANISM: Artificial Sequence
<220> FEATURE:
<223> OTHER INFORMATION: Sequence is SEQ. ID No. 7 preceded by a His tag
<220> FEATURE:
<221> NAME/KEY: REPEAT
<222> LOCATION: (18)..(47)
<223> OTHER INFORMATION: The series of residues from positions 18-47 may
      repeat 6, 7, 8, 9, 10, or n times
<220> FEATURE:
<221> NAME/KEY: MISC_FEATURE
<222> LOCATION: (20)..(20)
<223> OTHER INFORMATION: Xaa at position 20 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (30)..(30)
<223> OTHER INFORMATION: Xaa at position 30 may be V, Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (35)..(35)
<223> OTHER INFORMATION: Xaa at position 35 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (40)..(40)
<223> OTHER INFORMATION: Xaa at position 40 may be E or K
<220> FEATURE:
<221> NAME/KEY: MISC_FEATURE
<222> LOCATION: (45)..(45)
<223> OTHER INFORMATION: Xaa at position 45 may be V, Y,
      dihydroxyphenylalanine (DOPA), or 3, 4, 5-trihydroxyphenylalanine
      (TOPA)

<400> SEQUENCE: 4

His His His His His His His Asp Asp Asp Asp Lys Leu Asp Gly Thr
1               5                   10                  15
```

```
Leu Pro Gly Xaa Gly Val Pro Gly Lys Gly Val Pro Gly Xaa Gly Val
            20                  25                  30

Pro Gly Xaa Gly Val Pro Gly Xaa Gly Val Pro Gly Xaa Gly Val Pro
        35                  40                  45

Val Ala Asp Arg Gly Met Arg Leu Glu
    50                  55

<210> SEQ ID NO 5
<211> LENGTH: 62
<212> TYPE: PRT
<213> ORGANISM: Artificial Sequence
<220> FEATURE:
<223> OTHER INFORMATION: Sequence is SEQ ID No. 7 preceded by a T7 tag
      comprising SEQ ID NO. 13
<220> FEATURE:
<221> NAME/KEY: REPEAT
<222> LOCATION: (23)..(52)
<223> OTHER INFORMATION: The series of residues from positions 23 to 52
      may repeat 6, 7, 8, 9, 10, or n times
<220> FEATURE:
<221> NAME/KEY: MISC_FEATURE
<222> LOCATION: (25)..(25)
<223> OTHER INFORMATION: Xaa at position 25 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (35)..(35)
<223> OTHER INFORMATION: Xaa at position 35 may be V, Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (40)..(40)
<223> OTHER INFORMATION: Xaa at position 40 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (45)..(45)
<223> OTHER INFORMATION: Xaa at position 45 may be E or K
<220> FEATURE:
<221> NAME/KEY: MISC_FEATURE
<222> LOCATION: (50)..(50)
<223> OTHER INFORMATION: Xaa at position 50 may be V, Y,
      dihydroxyphenylalanine (DOPA), or 3, 4, 5-trihydroxyphenylalanine
      (TOPA)

<400> SEQUENCE: 5

Met Met Ala Ser Met Thr Gly Gly Gln Gln Met Gly Asp Asp Asp Asp
1               5                   10                  15

Lys Leu Asp Gly Thr Leu Pro Gly Xaa Gly Val Pro Gly Lys Gly Val
            20                  25                  30

Pro Gly Xaa Gly Val Pro Gly Xaa Gly Val Pro Gly Xaa Gly Val Pro
        35                  40                  45

Gly Xaa Gly Val Pro Val Ala Asp Arg Gly Met Arg Leu Glu
    50                  55                  60

<210> SEQ ID NO 6
<211> LENGTH: 69
<212> TYPE: PRT
<213> ORGANISM: Artificial Sequence
<220> FEATURE:
<223> OTHER INFORMATION: Sequence is SEQ. ID No. 4 preceded by a T7 tag
      comprising SEQ ID NO. 13
<220> FEATURE:
<221> NAME/KEY: REPEAT
<222> LOCATION: (30)..(59)
<223> OTHER INFORMATION: The series of residues from positions 30-59 may
      be repeated 8 times
```

```
<400> SEQUENCE: 6

Met Met Ala Ser Met Thr Gly Gly Gln Gln Met Gly His His His
1               5                   10                  15

His His His Asp Asp Asp Asp Lys Leu Asp Gly Thr Leu Pro Gly Tyr
                20                  25                  30

Gly Val Pro Gly Lys Gly Val Pro Gly Val Gly Val Pro Gly Tyr Gly
            35                  40                  45

Val Pro Gly Lys Gly Val Pro Gly Val Gly Val Pro Val Ala Asp Arg
    50                  55                  60

Gly Met Arg Leu Glu
65

<210> SEQ ID NO 7
<211> LENGTH: 50
<212> TYPE: PRT
<213> ORGANISM: Artificial Sequence
<220> FEATURE:
<223> OTHER INFORMATION: Sequence is SEQ. ID No. 2 preceded by a
      cleavage site
<220> FEATURE:
<221> NAME/KEY: REPEAT
<222> LOCATION: (11)..(40)
<223> OTHER INFORMATION: The series of residues from positions 11-40 may
      repeat 6, 7, 8, 9, 10, or n times
<220> FEATURE:
<221> NAME/KEY: MISC_FEATURE
<222> LOCATION: (12)..(12)
<223> OTHER INFORMATION: Xaa at position 12 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (23)..(23)
<223> OTHER INFORMATION: Xaa at position 23 may be V, Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (28)..(28)
<223> OTHER INFORMATION: Xaa at position 28 may be Y,
      dihydroxyphenylalanine (DOPA), or 3, 4, 5-trihydroxyphenylalanine
      (TOPA)
<220> FEATURE:
<221> NAME/KEY: MISC_FEATURE
<222> LOCATION: (33)..(33)
<223> OTHER INFORMATION: Xaa at position 33 may be E or K
<220> FEATURE:
<221> NAME/KEY: MISC_FEATURE
<222> LOCATION: (38)..(38)
<223> OTHER INFORMATION: Xaa at position 38 may be V, Y,
      dihydroxyphenylalanine (DOPA), or 3, 4, 5-trihydroxyphenylalanine
      (TOPA)

<400> SEQUENCE: 7

Asp Asp Asp Asp Lys Leu Asp Gly Thr Leu Pro Gly Xaa Gly Val Pro
1               5                   10                  15

Gly Lys Gly Val Pro Gly Xaa Gly Val Pro Gly Xaa Gly Val Pro Gly
            20                  25                  30

Xaa Gly Val Pro Gly Xaa Gly Val Pro Val Ala Asp Arg Gly Met Arg
        35                  40                  45

Leu Glu
    50

<210> SEQ ID NO 8
<211> LENGTH: 5
<212> TYPE: PRT
<213> ORGANISM: Artificial Sequence
```

```
<220> FEATURE:
<223> OTHER INFORMATION: Sequence per se is derived from human thought
<220> FEATURE:
<221> NAME/KEY: REPEAT
<222> LOCATION: (1)..(5)
<223> OTHER INFORMATION: The series of residues from positions 1-5 may
      be repeated at least 6 times
<220> FEATURE:
<221> NAME/KEY: MISC_FEATURE
<222> LOCATION: (4)..(4)
<223> OTHER INFORMATION: Xaa at position 4 may be E, K, Y, or Y in each
      of the repeated VPGXG sequences, with Y appearing in at least one
      of the repeated VPGXG sequences

<400> SEQUENCE: 8

Val Pro Gly Xaa Gly
1               5

<210> SEQ ID NO 9
<211> LENGTH: 45
<212> TYPE: PRT
<213> ORGANISM: Artificial Sequence
<220> FEATURE:
<223> OTHER INFORMATION: Possible variation of SEQ ID No. 2
<220> FEATURE:
<221> NAME/KEY: REPEAT
<222> LOCATION: (6)..(35)
<223> OTHER INFORMATION: Series of residues from positions 6-35 may
      repeat 6, 7, 8, 9, 10, or n times

<400> SEQUENCE: 9

Leu Asp Gly Thr Leu Pro Gly Tyr Gly Val Pro Gly Lys Gly Val Pro
1               5                   10                  15

Gly Val Gly Val Pro Gly Tyr Gly Val Pro Gly Lys Gly Val Pro Gly
            20                  25                  30

Val Gly Val Pro Val Ala Asp Arg Gly Met Arg Leu Glu
        35                  40                  45

<210> SEQ ID NO 10
<211> LENGTH: 5
<212> TYPE: PRT
<213> ORGANISM: Artificial Sequence
<220> FEATURE:
<223> OTHER INFORMATION: Sequence per se is derived from human thought

<400> SEQUENCE: 10

Leu Asp Gly Thr Leu
1               5

<210> SEQ ID NO 11
<211> LENGTH: 11
<212> TYPE: PRT
<213> ORGANISM: Artificial Sequence
<220> FEATURE:
<223> OTHER INFORMATION: Sequence per se is derived from human thought

<400> SEQUENCE: 11

Met Ser Lys Gly Pro Gly Val Asp Gly Thr Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Sequence per se is derived from human thought

<400> SEQUENCE: 12
```

```
Pro Val Ala Asp Arg Gly Met Arg Leu Glu
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Sequence is a T7 tag

<400> SEQUENCE: 13

Met Met Ala Ser Met Thr Gly Gly Gln Gln Met Gly
1               5                   10
```

PROTEIN-BASED ADHESIVES

PRIORITY

The present application is related to, claims the priority benefit of, and is a U.S. continuation-in-part patent application of, U.S. nonprovisional patent application Ser. No. 15/212,152, filed Jul. 15, 2016, which is related to, and claims the priority benefit of, U.S. provisional patent application Ser. No. 62/193,069, filed Jul. 15, 2015. The contents of each of the foregoing applications are incorporated herein by reference in their entirety.

GOVERNMENT RIGHTS

This invention was made with Government support under DMR1309787 awarded by the National Science Foundation. The Government has certain rights in the invention.

BACKGROUND

There has been a wealth of recent interest in the development of adhesive materials that function in wet or underwater environments. In particular, much of this focus has been placed on adhesive development for biomedical applications, as a suitable biomedical adhesive could have an immense impact on health and the economy. Each year, over 230 million major surgeries are performed worldwide, and over 12 million traumatic wounds are treated in the U.S. alone. Approximately 60% of these wounds are closed using mechanical methods such as sutures and staples. Sutures and staples have several disadvantages relative to adhesives, including patient discomfort, higher risk of infection, and the inherent damage to surrounding healthy tissue.

Current FDA-approved adhesives and sealants face several challenges. First, numerous adhesives exhibit toxic characteristics. For example, cyanoacrylate-based adhesives like Dermabond® and SurgiSeal® can only be applied topically due to carcinogenic degradation products. Fibrin sealants like Tisseel and Artiss are derived from blood sources and therefore carry the potential for blood-borne pathogen transmission. Poly(ethylene glycol) (PEG) adhesives are approved as a suture sealants but, due to intense swelling when wet, have the potential to cause moderate inflammatory responses. TissuGlu®, a following subcutaneous implantation, and, in clinical trials, seroma formation occurred in 22% of patients. More important, however, is that most of these adhesives do not possess strong adhesion in an excessively wet environment and are not approved for application in wound closure. In fact, many of these materials specifically advise to dry the application area as much as possible.

In approaching the challenge of developing a strong adhesive for wet applications, many researchers have been inspired by natural glues. Specifically, underwater application and bonding has been demonstrated with materials based on organisms such as sandcastle worms and mussels. Both of these organisms produce proteins containing the non-canonical amino acid 3,4-dihydroxyphenylalanine (DOPA), which has been shown to provide adhesion strength, even in wet environments. In the case of a mussel-mimetic polymer, underwater application was achieved by dissolving the polymer in a chloroform/methanol solution to maintain phase separation from the aqueous environment. The use of toxic organic solvents, however, is not appropriate for biomedical applications.

An alternative method for underwater application uses the phenomenon of coacervation, a form of aqueous liquid-liquid phase separation that is implicated in the adhesion mechanism of sandcastle worms, caddisfly larvae, and mussels. Adhesive coacervate materials mimicking both mussels and sandcastle worms have been developed. To form these coacervates, multiple components needed to be mixed in specific conditions and thus limited their overall applicability. As can be seen, there is a need for a strong adhesive that functions in a wet environment. It would also be desirable if this adhesive could be manipulated in forming a strong seal in the desired environment. It would be further desirable if the adhesive was also non-toxic and may be used in biomedical applications.

BRIEF DESCRIPTION OF THE SEQUENCE LISTING

SEQ ID NO. 1 is an artificial sequence of an elastin-like polypeptide according to the subject disclosure that comprises the repeating sequence $PGX_1GVPGKGVPGX_2GVPGX_1GVPGX_3GVPGX_2GV$, wherein each $X_1$ is selected from the group consisting of tyrosine (Y), dihydroxyphenylalanine (DOPA), and 3,4,5-trihydroxyphenylalanine (TOPA), wherein each $X_2$ is selected from the group consisting of valine (V), Y, DOPA, and TOPA, wherein each $X_3$ is selected from the group consisting of glutamic acid (E) and lysine (K), and wherein the sequence repeats 6, 7, 8, 9, 10, or n (5 or fewer or 11 or greater) times;

SEQ ID NO. 2 is an artificial sequence of an elastin-like polypeptide according to the subject disclosure that comprises SEQ ID NO. 1 preceded by SEQ ID NO. 10 and followed by SEQ ID NO. 12;

SEQ ID NO. 3 is an artificial sequence of an elastin-like polypeptide according to the subject disclosure that comprises SEQ ID NO. 1 preceded by SEQ ID NO. 11 and followed by SEQ ID NO. 12;

SEQ ID NO. 4 is an artificial sequence of an elastin-like polypeptide according to the subject disclosure that comprises SEQ ID NO. 7 preceded by a His tag having the sequence HHHHHHH;

SEQ ID NO. 5 is an artificial sequence of an elastin-like polypeptide according to the subject disclosure that comprises SEQ ID NO. 7 preceded by a T7 tag having the sequence of SEQ ID NO. 13;

SEQ ID NO. 6 is an artificial sequence of an elastin-like polypeptide according to the subject disclosure that comprises SEQ ID NO. 4 preceded by a T7 tag having the sequence of SEQ ID NO. 13, and wherein the residues of SEQ ID NO. 1 within SEQ ID NO. 4 are repeated 8 times;

SEQ ID NO. 7 is an artificial sequence of an elastin-like polypeptide according to the subject disclosure that comprises SEQ ID NO. 2 preceded by a cleavage site having the sequence DDDDK;

SEQ ID NO. 8 is a repeated amino acid sequence according to the subject disclosure that comprises the sequence VPGXG, wherein the amino acid sequence is repeated at least 5 times within the elastin-like polypeptide, X is selected from the group consisting of glutamic acid (E), lysine (K), valine (V), and tyrosine (Y), and Y appears at least once within the elastin-like polypeptide;

SEQ ID NO. 9 is an artificial sequence of an elastin-like polypeptide according to the subject disclosure that comprises a possible variation of SEQ ID NO. 2, wherein $X_1$ is Y, $X_2$ is V, and $X_3$ is K;

SEQ ID NO. 10 is an artificial sequence according to the subject disclosure that comprises the sequence LDGTL;

SEQ ID NO. 11 is an artificial sequence according to the subject disclosure that comprises the sequence MSKG-PGVDGTL;

SEQ ID NO. 12 is an artificial sequence according to the subject disclosure that comprises the sequence PVADRG-MRLE; and SEQ ID NO. 13 is a T7 tag having the sequence MMASMTGGQQMG.

In addition to the foregoing, a written Sequence Listing for the above-described artificial sequences is appended hereto and the same Sequence Listing is provided in computer readable form encoded in a file filed herewith and herein incorporated by reference. The information recorded in computer readable form is identical to the written Sequence Listing provided herein, pursuant to 37 C.F.R. § 1.821(f).

BRIEF SUMMARY

The present disclosure includes disclosure of an elastin-like polypeptide having a repeating sequence comprising SEQ ID No. 1, wherein each $X_1$ is selected from the group consisting of tyrosine (Y), dihydroxyphenylalanine (DOPA), and 3,4,5-trihydroxyphenylalanine (TOPA), wherein each $X_2$ is selected from the group consisting of valine (V), Y, DOPA, and TOPA, wherein each $X_3$ is selected from the group consisting of glutamic acid (E) and lysine (K), and wherein the sequence repeats 6, 7, 8, 9, 10, or n (5 or fewer or 11 or greater) times. The repeating sequence can be initially preceded by the sequence comprising SEQ ID No. 10 or SEQ ID No. 11, as may be desired. The repeating sequence can ultimately be followed by the sequence comprising SEQ ID No. 12, as may be desired.

The present disclosure includes disclosure of an elastin-like polypeptide having a sequence comprising SEQ ID No. 2, wherein each $X_1$ is selected from the group consisting of tyrosine (Y), dihydroxyphenylalanine (DOPA), and 3,4,5-trihydroxyphenylalanine (TOPA), wherein each $X_2$ is selected from the group consisting of valine (V), Y, DOPA, and TOPA, wherein each $X_3$ is selected from the group consisting of glutamic acid (E) and lysine (K), and wherein n is at or between 6 and 10, or wherein n is a different number, such as 11 or higher or 5 or lower.

The present disclosure includes disclosure of an elastin-like polypeptide, wherein n is 8, so that the elastin-like polypeptide has a sequence comprising SEQ ID No. 2, wherein the repeating SEQ ID No. 1 thereof is repeated 8 times.

The present disclosure includes disclosure of an elastin-like polypeptide, preceded by a cleavage site having the sequence DDDDK so that the elastin-like polypeptide has a sequence comprising SEQ ID No. 7.

The present disclosure includes disclosure of an elastin-like polypeptide, wherein the cleavage site is preceded by an His tag having the sequence HHHHHHH, so that the elastin-like polypeptide has a sequence comprising SEQ ID No. 4.

The present disclosure includes disclosure of an elastin-like polypeptide, wherein the His tag is preceded by a T7 tag having the sequence comprising SEQ ID No. 13, so that the elastin-like polypeptide has a sequence comprising SEQ ID No. 5.

The present disclosure includes disclosure of an elastin-like polypeptide, having a lower critical solution temperature (LCST) at or between 25° C. and 37° C.

The present disclosure includes disclosure of an elastin-like polypeptide, having a sequence comprising SEQ ID No. 9.

The present disclosure includes disclosure of an elastin-like polypeptide, wherein at least one $X_1$ comprises Y, and wherein the at least one Y is replaced by DOPA or TOPA during exposure to tyrosinase.

The present disclosure includes disclosure of an elastin-like polypeptide, wherein n=8, and wherein each $X_1$ comprises Y.

The present disclosure includes disclosure of an elastin-like polypeptide, capable of adhering to a substrate when applied to said substrate under wet conditions.

The present disclosure includes disclosure of an elastin-like polypeptide, wherein each $X_2$ is V, and wherein each $X_3$ is K.

The present disclosure includes disclosure of an elastin-like polypeptide, wherein the first L within the sequence is replaced with SEQ ID No. 11, so that the elastin-like polypeptide has a sequence comprising SEQ ID No. 3.

The present disclosure includes disclosure of an elastin-like polypeptide comprising a repeated amino acid sequence comprising SEQ ID No. 8, wherein the repeated amino acid sequence is repeated at least five times within the elastin-like polypeptide, wherein X is selected from the group consisting of glutamic acid (E), lysine (K), valine (V), and tyrosine (Y), and wherein Y appears at least once within the elastin-like polypeptide.

The present disclosure includes disclosure of an elastin-like polypeptide, wherein at least one X also comprises at least one V.

The present disclosure includes disclosure of an elastin-like polypeptide, wherein the at least one Y is replaced by DOPA or TOPA during exposure to tyrosinase.

The present disclosure includes disclosure of an elastin-like polypeptide, capable of adhering to a substrate when applied to said substrate under wet conditions.

The present disclosure includes disclosure of an elastin-like polypeptide, capable of forming a coacervate in the wet conditions at 37° C.

The present disclosure includes disclosure of an elastin-like polypeptide having a sequence comprising a variation of SEQ ID No. 2, wherein $X_2$ is V, $X_3$ is K, and each $X_1$ is selected from the group consisting of tyrosine (Y), dihydroxyphenylalanine (DOPA), and 3,4,5-trihydroxyphenylalanine (TOPA).

The present disclosure includes disclosure of an elastin-like polypeptide, wherein n is at or between 6 and 10.

The present disclosure includes disclosure of an elastin-like polypeptide, wherein n is 8, so that the elastin-like polypeptide has a sequence comprising a variation of SEQ ID No. 2, wherein $X_2$ is V, $X_3$ is K, and n is 8.

The present disclosure includes disclosure of an elastin-like polypeptide, preceded by a cleavage site having the sequence DDDDK so that the elastin-like polypeptide has a sequence comprising a variation of SEQ ID No. 7, wherein $X_2$ is V and $X_3$ is K.

The present disclosure includes disclosure of an elastin-like polypeptide, wherein the cleavage site is preceded by an His tag having the sequence HHHHHHH, so that the elastin-like polypeptide has a sequence comprising a variation of SEQ ID No. 4, wherein $X_2$ is V and $X_3$ is K.

The present disclosure includes disclosure of an elastin-like polypeptide, wherein the His tag is preceded by a T7 tag having the sequence comprising SEQ ID No. 13, so that the elastin-like polypeptide has a sequence comprising a variation of SEQ ID No. 5, wherein $X_2$ is V and $X_3$ is K.

The present disclosure includes disclosure of an elastin-like polypeptide, having a lower critical solution temperature (LCST) at or between 25° C. and 37° C.

The present disclosure includes disclosure of an elastin-like polypeptide, having a sequence comprising SEQ ID No. 9.

The present disclosure includes disclosure of an elastin-like polypeptide, wherein at least one $X_1$ comprises Y, and wherein the at least one Y is replaced by DOPA or TOPA during exposure to tyrosinase.

The present disclosure includes disclosure of an elastin-like polypeptide, wherein n=8, and wherein each $X_1$ comprises Y.

The present disclosure includes disclosure of an elastin-like polypeptide, capable of adhering to a substrate when applied to said substrate under wet conditions.

The present disclosure includes disclosure of an elastin-like polypeptide comprising a repeated amino acid sequence comprising SEQ ID No. 8, wherein the repeated amino acid sequence is repeated at least five times within the elastin-like polypeptide, wherein X is selected from the group consisting of lysine (K), valine (V), and tyrosine (Y), and wherein each of K, V, and Y appears at least once within the elastin-like polypeptide.

The present disclosure includes disclosure of an elastin-like polypeptide, wherein at least one X comprises at least one Y.

The present disclosure includes disclosure of an elastin-like polypeptide, wherein the at least one Y is replaced by DOPA or TOPA during exposure to tyrosinase.

The present disclosure includes disclosure of an elastin-like polypeptide, capable of adhering to a substrate when applied to said substrate under wet conditions.

The present disclosure includes disclosure of an elastin-like polypeptide, capable of forming a coacervate in the wet conditions at 37° C.

The present disclosure includes disclosure of a method of generating a polypeptide configured for wet adhesion, comprising the steps of providing an initial polypeptide having a sequence comprising SEQ ID No. 9, and dissolving the initial polypeptide in a buffer comprising a tyrosinase to form a mixture so that least one tyrosine of the initial polypeptide is converted to dihydroxyphenylalanine (DOPA) within the mixture.

The present disclosure includes disclosure of a method of generating a polypeptide configured for wet adhesion, wherein the step of further reacting comprises converting at least one DOPA to 3,4,5-trihydroxyphenylalanine (TOPA).

The present disclosure includes disclosure of a method of generating a polypeptide configured for wet adhesion, further comprising the step of adding an acid to the mixture after a first period of time has elapsed so to cease further conversion of tyrosine to DOPA.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 1A shows a diagram of converting an ELP to a modified ELP, according to an exemplary embodiment of the present disclosure;

FIG. 1B shows an amino acid sequence of an ELP with a T7 tag, a His tag, and a cleavage site, according to an exemplary embodiment of the present disclosure;

FIG. 4A shows relative adhesion strengths of BSA, Tisseel, and two ELPs in a dry environment, according to an exemplary embodiment of the present disclosure;

FIG. 4B shows relative adhesion strengths of BSA, Tisseel, and two ELPs in a humid (also referred to as a wet) environment, according to an exemplary embodiment of the present disclosure;

FIG. 6A shows a chart of MALDI-TOF spectra of an $ELY_{16}$, according to an exemplary embodiment of the present disclosure;

FIG. 6B shows a chart of MALDI-TOF spectra of a $mELY_{16}$, according to an exemplary embodiment of the present disclosure;

FIG. 7 shows a table of amino acid analyses of two ELPs, according to exemplary embodiments of the present disclosure;

Figure 2A:
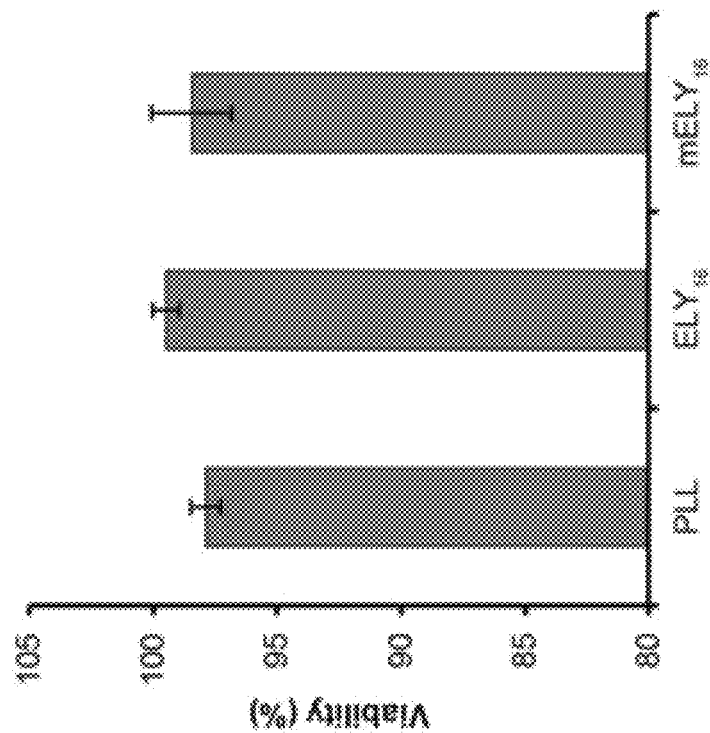
FIG. 2A shows a chart of relative viabilities of NIH/3T3 fibroblasts in the presence of PLL, an ELP identified as $ELY_{16}$, and a modified ELP identified as $mELY_{16}$, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Broadly, the present disclosure provides elastin-like polypeptides (ELPs) having adhesive properties better than other biological glues known in the art. The ELP's of the present disclosure are advantageous for use in wet adhesion. Additionally, the ELP's of the present disclosure show high cytocompatability and are appropriate for use in biomedical applications. The ELP's of the present disclosure may be designed to have a desired lower critical solution temperature (LCST) at which coacervation occurs. The ELP's may be designed to have an LCST that is consistent with the desired use of the adhesive.

Current adhesives in the art need to be applied to a dry or almost dry surface in order to have the adhesive strength required for many applications, particularly those in the biomedical area. For example, it is desirable to use adhesives in place of staples or sutures. However, the adhesives currently being used are limited to applications where the surfaces to be bonded can be dried. In contrast, the ELP adhesives of the present disclosure may be applied underwater, in high humidity and on wet tissue and still form a strong adhesive bond.

In one embodiment of the present disclosure, there is provided an ELP having the sequence comprising a variation of SEQ ID No. 9 comprising four repetitions of SEQ ID No. 12. In an illustrative embodiment, n may be from about 6 to about 10, including 6, 7, 8, 9, or 10. In at least one embodiment, n may be 8. The sequence in parenthesis is an elastin-like peptide region. In the sequence above, the number of tyrosine (Y), lysine (K) and valine (V) residues may be modified in order to modify the LCST. The LCST may be a function of hydrophobicity, length of the peptide, pH, concentration of the ELP and/or the amount of salt present.

For reference, the following amino acid abbreviations and names may be identified herein as applying to one or more polypeptides or proteins of the present disclosure:

| Three-letter Abbreviation | Single-letter Abbreviation | Amino Acid Name |
| --- | --- | --- |
| Ala | A | Alanine |
| Arg | R | Arginine |
| Asn | N | Asparagine |
| Asp | D | Aspartic acid (Aspartate) |
| Cys | C | Cysteine |
| Gln | Q | Glutamine |
| Glu | E | Glutamic acid (Glutamate) |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |
| Asx | B | Aspartic acid or Asparagine |
| Glx | Z | Glutamine or Glutamic acid |
| Xaa | X | (any amino acid, or a group of amino acids, as may be referenced herein) |

In one embodiment of the present disclosure, hydrophobicity is used to determine the LCST and the coacervation temperature. The coacervation temperature is the temperature at which the ELPs undergo a phase transition from solution to an adhesive. There are several different useful for measuring hydrophobicity. For the examples herein, hydrophobicity was determined using the scale developed by DW Urry. In short, Urry made ELPs with each individual amino acid as a guest residue and determined the temperature at which phase transition behavior occurred (i.e., the LCST). He then arranged all of the amino acids in order of their LCSTs. In essence, this is an exemplary way to order the amino acids in terms of hydrophobicity. The ELPs of the present disclosure were designed to have guest residues with a number-average LCST somewhere between 25° C. and 37° C. Alternatively, other hydrophobicity scales may be used. It will be appreciated that those skilled in the art are familiar with such scales and can apply them to the present disclosure without undue experimentation.

In another embodiment of the present disclosure, the ELPs comprise tyrosine. In another embodiment some or all of the tyrosine residues are replaced by DOPA and/or TOPA, in any combination thereof. The DOPA and TOPA may be formed enzymatically through treatment with an enzyme such as a tyrosinase. Alternative, they may be formed chemically using methods well known in the art. Another method would be to produce the ELPs synthetically, adding DOPA and TOPA to the peptides. In another method, the ELPs of the present disclosure may be produced recombinantly and using methods known in the art, substituting DOPA and/or TOPA for the tyrosine.

Certain embodiments of the disclosure may be more clearly understood through the following non-limiting examples.

EXAMPLES

Materials and Methods

Reagents:

All chemicals were purchased from Sigma-Aldrich (St. Louis, Mo.) or Avantor Performance Materials (Center Valley, Pa.) unless stated otherwise. Water was ultra-purified with a Milli-Q ultra-purification system (Millipore, Billerica, Mass.). NIH/3T3 fibroblasts were a generous gift from Dr. Alyssa Panitch (Purdue University). Tisseel was generously donated by Baxter BioSurgery (Deerfield, Ill.).

Protein Design and Cloning:

The elastin-like polypeptide (ELP) labeled as $ELY_{16}$ was designed with Geneious software (Biomatters Inc., San Francisco, Calif.) using the repeated amino acid sequence Val-Pro-Gly-Xaa-Gly; the guest residues Xaa were evenly divided among Tyr, Lys, and Val. The complete amino acid sequence for full-length $ELY_{16}$ is shown in FIG. 1B. Cloning was performed using standard techniques (Ausubel F M et al., editors. Current Protocols in Molecular Biology. New York: John Wiley & Sons; 2003) and a scheme modified from one previously developed (Renner, J N et al., Protein Expr Purif 2012; 82:90-6). The new scheme utilized AgeI and AvaI restriction enzymes (New England Biolabs, Ipswich, Mass.) to achieve seamless repeats of the elastin-like sequence.

Protein Expression and Purification:

$ELY_{16}$ was transformed into the Rosetta2(DE3)pLysS *E. coli* expression host (EMD Chemicals, Gibbstown, N.J.). Bacterial colonies were inoculated into 2xYT medium containing 50 µg/mL kanamycin and 34 µg/mL chloramphenicol and grown 16-18 h at 37° C. and 300 rpm. The overnight culture was diluted 1:250 for expression in a 14 L-capacity fermenter (BioFlo 100, New Brunswick Scientific, Enfield, Conn.) with 10 L of Terrific Broth (TB). When the optical density (OD) at 600 nm reached 5-6, protein expression was induced by the addition of isopropyl β-D-1-thiogalactopyranoside (IPTG, EMD Chemicals) at a final concentration of 2.5 mM. Upon reaching stationary phase, cells were harvested by centrifugation and immediately resuspended in Buffer B (8 M urea, 100 mM $NaH_2PO_4$, 100 mM Tris-Cl, pH 8.0) before being frozen at −80° C.

Purification was performed by a salting and heating method that was modified from a previously described protocol (Renner, J N et al., Biomacromolecules 2012; 13:3678-85; Kim, Y et al., Biomater Sci 2014; 2:1110-9). Cells were lysed by multiple freeze-thaw cycles in combination with sonication (Misonix XL-2000, Qsonica, Newtown, Conn.) for 1 min followed by a 1 min incubation on ice. Total sonication time was at least 2 h. The cell lysate was then centrifuged at 10000 g for 45 min and 4° C. to remove the cell debris. To salt out undesired proteins, 10% (w/v) ammonium sulfate was added to the cleared supernatant. The mixture was incubated on ice for 310 min followed by centrifugation for 45 min at 10000 g and 4° C. The supernatant was decanted from the pellet, and an additional 10% (w/v) ammonium sulfate was added to precipitate $ELY_{16}$. The solution was incubated on ice and centrifuged as before. The pellet was then resuspended in water at 500 mg/mL based on wet weight, heated to 80° C., vortexed, and heated again to 80° C. The heated solution was centrifuged for 45 min at 10000 g and 25° C., and the supernatant was dialyzed extensively against reverse osmosis water at 10° C. before lyophilization.

Expression and purification of $ELY_{16}$ were confirmed by sodium dodecyl sulfate-polyacrylamide gel electrophoresis (SDS-PAGE) and Western blot using standard techniques (Bonifacino J S et al., editors. Current Protocols in Cell Biology. New York: John Wiley & Sons; 2002). SDS-PAGE gels were stained with Coomassie Brilliant Blue R-250. The protein was detected in the Western blot using an anti-T7 tag antibody conjugated to horseradish peroxidase (EMD Chemicals, Gibbstown, N.J.) in combination with a 1-component 3,3',5,5'-tetramethylbenzidine (TMB) colorimetric substrate (Kirkegaard & Perry Laboratories, Gaithersburg, Md.). Purity was assessed using densitometry analysis with ImageJ software (NIH, Bethesda, Md.) (Abramoff, M D et al., Biophotonics Int 2004; 11:36-41).

The molecular weight was confirmed using matrix-assisted laser desorption/ionization-time of flight (MALDI-TOF) (Dr. Connie Bonham, Campus-Wide Mass Spectrometry Center, Purdue University) with sinapinic acid as the matrix. Briefly, the MALDI mass spectra were obtained on a Voyager DE-Pro TOF mass spectrometer (Applied Biosystems, Framingham, Mass.) in the linear mode with delayed extraction. Positive-ion spectra were obtained with an acceleration voltage of 25000 V.

The amino acid composition was verified with amino acid analysis (John Schulze, Molecular Structure Facility, University of California, Davis). Briefly, the sample underwent liquid phase hydrolysis in 2 N HCl/1% phenol at 110° C. for 24 h before being dried. The sample was then dissolved in norleucine dilution buffer to a final volume of 1 mL, vortexed, and spun down. Injection volume was 50 µL at a 2.0 nmol scale.

Tyrosinase Modification:

To convert tyrosine residues to DOPA, $ELY_{16}$ was dissolved at 2 mg/mL in 0.1 M sodium acetate buffer with 0.1 M ascorbic acid, pH 5.5. Mushroom tyrosinase was added to a final concentration of 150 U/mL, and the mixture was incubated at 37° C. and 200 rpm for 8 h. Enzyme activity was halted with 0.2 mL of 6 N HCl per mL of reaction as described previously (Marumo K & Waite J H, Biochem Biophys Acta 1986; 872:98-103.). The tyrosinase-modified $ELY_{16}$ ($mELY_{16}$) solution was dialyzed extensively in 5% acetic acid at 4° C. and lyophilized.

The extent of conversion was measured with difference spectrophotometry (Waite J H, Anal Chem 1984; 56:1935-9) and comparison to standard solutions of L-DOPA. The increase in molecular weight due to conversion was confirmed by MALDI-TOF and SDS-PAGE. DOPA content was also assessed with amino acid analysis using a procedure similar to that described above with the modifications of using a 5.0 nmol scale and S-2-aminoethyl-L-cysteine as a diluent. The DOPA elution peak was compared with that of an L-DOPA control solution.

Protein Adsorption to Coverslips:

Acid-washed coverslips (12 mm diameter, VWR, Radnor, Pa.) were incubated overnight at 4° C. with $ELY_{16}$, $mELY_{16}$, or bovine serum albumin (BSA, Fraction V, EMD Chemicals, Gibbstown, N.J.) dissolved at 1 mg/mL in water. Protein surface density was measured by washing coverslips three times with MilliQ water and performing a bicinchoninic acid (BCA) colorimetric assay. Separate standard solutions for $ELY_{16}$ and BSA were used to determine adsorbed protein concentration. Four replicates were tested for each sample.

Cell Culture:

NIH/3T3 fibroblasts were generously donated by Dr. Alyssa Panitch (Purdue University). Fibroblasts were cultured at 37° C. and 5% CO2 in high-glucose Dulbecco's Modified Eagle's Medium (DMEM) supplemented with 100 U/mL penicillin-streptomycin (Gibco, Carlsbad, Calif.) and 10% bovine calf serum. Cells were subcultured at 60-80% confluency.

Cytocompatibility Testing:

Coverslips coated in adsorbed protein sterilized by incubation in 70% ethanol for 5 min, blocked in sterile-filtered BSA (1 mg/mL in water) for 30 min, and rinsed with phosphate-buffered saline (PBS, 4.2 mM $NaHPO_4$, 0.8 mM $KH_2PO_4$, 50 mM NaCl, pH 7.4). Fibroblasts were seeded onto coverslips at 2500 cells per $cm^2$ in a 24-well plate (BD Falcon, Durham, N.C.). For a positive control, acid-washed coverslips were incubated for 5 min in 0.01% poly-L-lysine (PLL, Trevigen, Gaithersburg, Md.) then rinsed three times in PBS. Images were taken with a Nikon Ti-E C-1 Plus microscope. All groups were tested in triplicate.

To assess cell viability, cells were cultured for 2 days and tested with a LIVE/DEAD viability/cytotoxicity kit (Molecular Probes, Carlsbad, Calif.). Cells were incubated in staining solution (1.5 μM ethidium homodimer-1 and 0.5 μM calcein acetoxymethyl ester (calcein AM) in PBS), rinsed three times with PBS, and imaged with a 10× objective. All PBS was supplemented with 0.01% $CaCl_2$ and 0.01% $MgCl_2$ to prevent cell detachment. As a negative control, cells on PLL were incubated in 70% ethanol for 30 min at 37° C. prior to staining. Cells were counted using NIS-Elements software (Nikon, Tokyo, Japan), and at least 90 cells were counted per replicate. Viability was calculated as the number of living cells divided by the total number of cells in each replicate.

Cell morphology was assessed via actin staining. After culturing for 2 days, cells were fixed in ice-cold acetone for 1 min and then washed three times with filtered PBS. Coverslips were then incubated for 20 min with Alexa Fluor 488 phalloidin (Molecular Probes, Carlsbad, Calif.) at a 1:40 dilution in PBS. Following three 10 min washes with PBS, cells were then counterstained for 30 min with DRAQ5 (Biostatus Limited, Leicestershire, UK) diluted 1:500 in PBS. Finally, coverslips were rinsed twice in PBS, mounted with Vectashield (Vector Laboratories), and sealed with nail polish. Confocal imaging was performed with EZ-C1 software using a 40× objective.

Turbidity Testing:

Lower critical solution temperatures (LCSTs) of $ELY_{16}$ and $ELY_{16}$ were assessed using turbidity readings from a Crystal16 (Technobis Group, Alkmaar, the Netherlands). Protein samples were held at 10° C. for 15 min, ramped at 1° C./min to 50° C., then held at 50° C. for 2 min. Light transmission data was recorded and normalized to the maximum transmission for each sample. The LCST was calculated as the inflection point of the transmission vs. temperature curve.

Lap Shear Adhesion:

Aluminum adherends were prepared and cleaned using ASTM standard D2651-01 (Standard D2651: Preparation of metal surfaces for adhesive bonding. West Conshohocken, Pa.: ASTM International; 2008). Bulk lap shear adhesion bonding was tested with a modified version of the ASTM D1002 standard, as previously described (Jenkins, C L et al., ACS Appl Mater Interfaces 2013; 5:5091-6; Standard D1002: Apparent shear strength of single-lap-joint adhesively bonded metal specimens by tension loading (metal-to-metal). West Conshohocken, Pa.: ASTM International; 2010). Briefly, protein was resuspended at 150 mg/mL in water, and 5 μL of this solution was spread onto each aluminum adherend. Tisseel was prepared according to the manufacturer's instructions and tested by applying an equivalent total mass of protein (1.5 mg per test) based on the stated protein content of Tisseel. Adherends were overlapped with an area of 1.2 cm×1.2 cm and were cured for 24 h at 37° C. Bond strengths were quantified using an Instron 5544 Materials Testing System (Norwood, Mass.) with a 2000 N load cell and a loading rate of 2 mm/min. Maximum force was divided by overlap area to determine the adhesion strength. Each condition was tested with at least 5 samples.

For humid curing, adherends were covered with a layer of damp paper towels followed by a layer of plastic wrap to prevent them from drying. For underwater curing, protein solution (either $ELY_{16}$ or $mELY_{16}$) was adjusted to pH 7.5. Aluminum adherends were placed in a PBS bath at 37° C. Protein solution (10 μL) was applied to one adherend, and the other adherend was overlapped as before. For underwater testing, at least 7 samples were tested for each group.

Statistical Analysis:

Data are represented as the mean±the standard deviation. All data were first examined for outliers using Grubbs' test; any outliers were discarded from further analysis. Next, Levene's test was used to assess equality of variances, and data were analyzed with one-way analysis of variance (ANOVA) followed by Tukey's Honestly Significant Difference (HSD) or the Games-Howell (for unequal variances) post hoc test. Finally, the normality of the ANOVA residuals was assessed with the Kolmogorov-Smirnov test. If the residuals were not normally distributed, the original data were transformed with the Box-Cox method, and the analysis was repeated on the transformed data. If only two groups were being compared, an unpaired t-test was used instead of ANOVA to assess statistical difference. All statistical analyses were performed with GraphPad online software (La Jolla, Calif.) or Minitab 17 (State College, Pa.). A p-value ≤0.05 was considered significant.

Results

Adhesive Protein Design and Production: The goal of this study was to create a cytocompatible adhesive with underwater functionality (FIG. 1A). FIG. 1A shows a schematic of material design, with a tyrosine-rich ELP referred to as $ELY_{16}$ is expressed in E. coli. Using mushroom tyrosinase, tyrosines are then converted to DOPA, as referenced in further detail herein, to create an adhesive protein, $mELY_{16}$, which can form a crosslinked adhesive material.

To achieve this goal, an ELP with a mixture of three guest residues (tyrosine, lysine, and valine) and a lower critical solution temperature (LCST) near body temperature was designed; the LCST was calculated based on the hydrophobicity scale developed by Urry (Urry, D W et al., J Am Chem Soc 1991; 113:4346-8; Urry, D W, J Phys Chem B 1991; 101:11007-28). Tyrosine was chosen as a precursor to DOPA. Lysine was chosen because numerous studies have suggested that it also contributes to wet adhesion strength in mussels. Valine was included as a third guest residue to balance out hydrophobicity. The final exemplary amino acid sequence is shown in FIG. 1B. The ELP was named $ELY_{16}$ to indicate that it contains 16 tyrosine (Y) residues available for conversion to DOPA. The final protein contains an N-terminal T7 tag, a 7×His tag, and an enterokinase cleavage site followed by an elastin-like domain based on the repeated pentapeptide VPGXG. Guest residues (X) of the pentapeptides are shown in bold in FIG. 1B, which can be any number of residues referenced herein. Tyrosine residues available for conversion to DOPA are underlined in FIG. 1B.

Figure 1C:
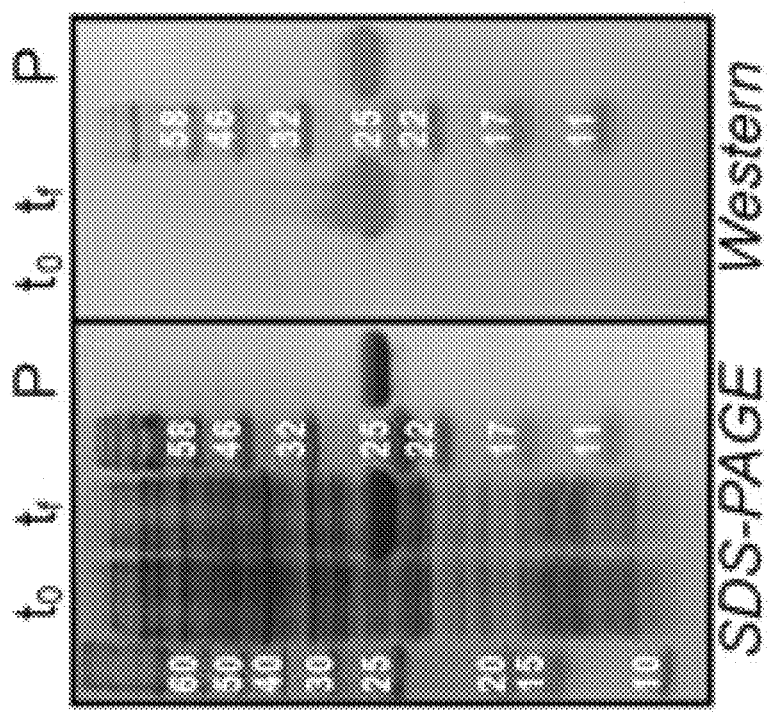
FIG. 1C shows a SDS-PAGE gel and a Western blot of an ELP, according to an exemplary embodiment of the present disclosure.

ELY$_{16}$ was highly over-expressed in a 14 L fermentor and then purified using a salting and heating method common to resilin-like polypeptides (Su, R S-C et al., Acta Biomater 2014; 10:1601-11). FIG. 1C shows expression and purification of ELY$_{16}$. SDS-PAGE gel and Western blot showing pre-induction (t0) and harvest (tf) expression samples, as well as purified protein (P). ELY$_{16}$ runs near its expected molecular weight of 25.548 kDa, as indicated by the standard protein ladders (bband weights labeled in kDa). Although the salting and heating method is not traditionally used for ELPs, it produced pure protein very efficiently with a final yield of 220 mg per liter of culture and >98% purity. MALDI-TOF and amino acid analysis confirmed protein identity (see also FIGS. 6 and 7).

Tyrosinase Catalyzed Conversion of TYR to DOPA: Mushroom tyrosinase was used to convert the tyrosine residues in ELY$_{16}$ to adhesive DOPA residues. The new ELP with the DOPA residues was designated mELY$_{16}$. Several methods were used to confirm a successful reaction with tyrosinase, including amino acid analysis, difference spectrophotometry (Waite, J H, Anal Chem 1984; 56:1935-9), SDS-PAGE, and MALDI-TOF. Amino acid analysis was used to assess the loss of tyrosine residues, from which a conversion percent can be calculated. As seen in FIG. 7, which includes a tabular amino acid analysis of ELY$_{16}$ and mELY$_{16}$, the molarity of tyrosine was reduced from 5.7% in ELY$_{16}$ to 0.7% in mELY$_{16}$, a conversion of 88%.

In contrast to amino acid analysis, difference spectrophotometry measures the difference in absorbance that results from the chelation of borate by DOPA. Using this method, a conversion of 54% of tyrosine to DOPA was measured. There are several reasons that difference spectrophotometry might estimate a lower conversion. First, because difference spectrophotometry relies on the presence of the reduced form of DOPA to chelate borate, it will underestimate DOPA concentration when DOPA has been oxidized. Furthermore, although this method has been validated for use with DOPA, its effectiveness has not been assessed in the presence of reaction side products such as 3,4,5-trihydroxyphenylalanine (TOPA).

Figure 8:
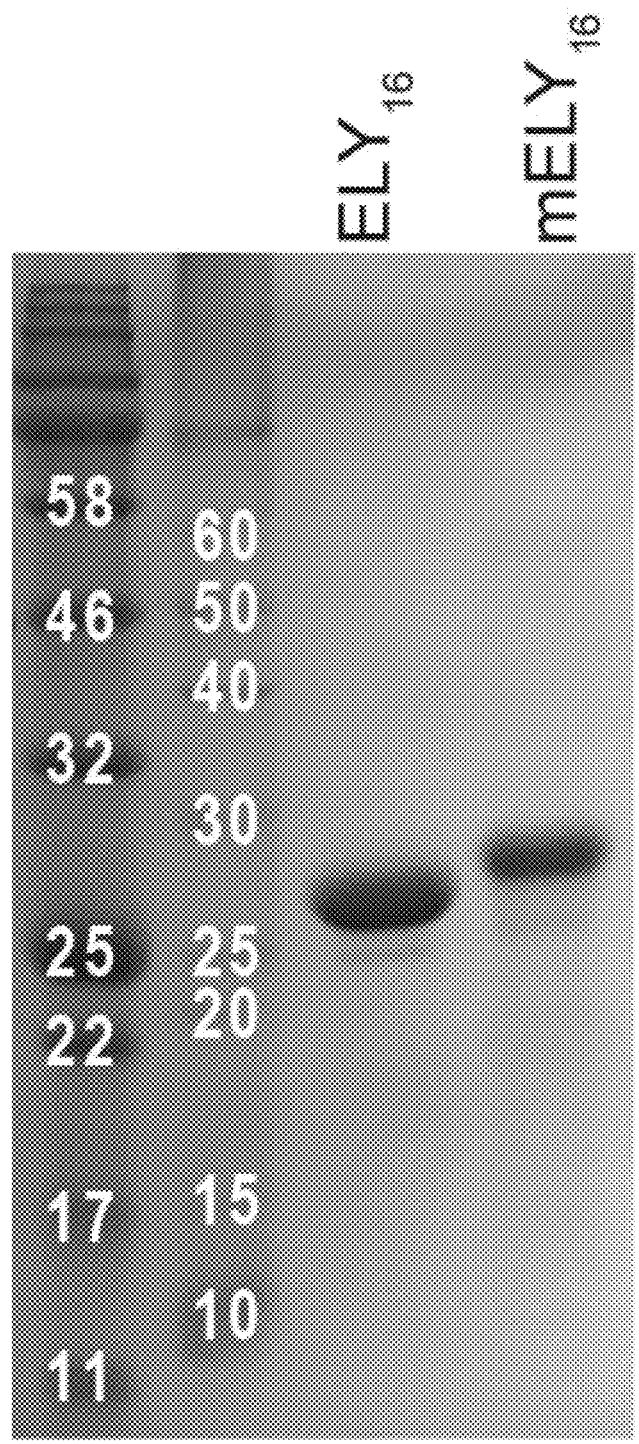
FIG. 8 shows an SDS-PAGE gel showing conversion of an ELP to a modified ELP, according to an exemplary embodiment of the present disclosure.

Finally, the change in molecular weight from converting ELY$_{16}$ to mELY$_{16}$ was assessed. On an SDS-PAGE gel shown in FIG. 8 (a SDS-PAGE gel showing that conversion of ELY$_{16}$ to mELY$_{16}$ significantly increases its molecular weight), mELY$_{16}$ ran distinctly higher than ELY$_{16}$, indicating that the molecular weight increased significantly with tyrosinase conversion. The change in molecular weight was quantitatively assessed with MALDI-TOF as shown in FIG. 6, which shows MALDI-TOF spectra of ELY$_{16}$ and mELY$_{16}$. Peaks near 7274 are bacterial contaminant proteins that often persist through purification procedures.

The spectrum for mELY$_{16}$ shows a peak with a broad distribution centered around 25925 Da. This value is greater than the molecular weight one would expect if all of the tyrosines were converted to DOPA. However, tyrosinase is able to further oxidize DOPA to higher-molecular-weight TOPA (Taylor, S W, Anal Biochem 2002; 302:70-4; Burzio, L A & Waite, J H, Anal Biochem 2002; 306:108-14); thus, mELY$_{16}$ could contain a mixture of tyrosine, DOPA, and TOPA.

Figure 2B:
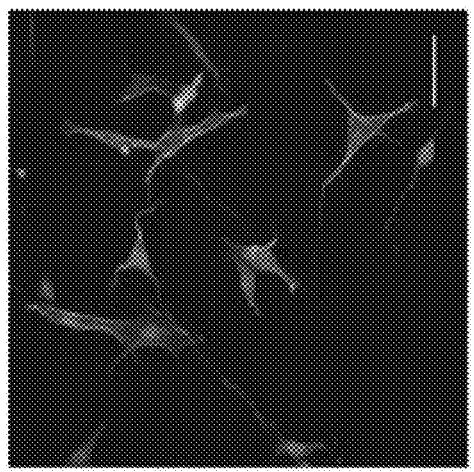
FIG. 2B shows photographs of NIH/3T3 fibroblasts cultured in the presence of PLL, an ELY, and a modified ELY, according to an exemplary embodiment of the present disclosure.
Figure 2B:
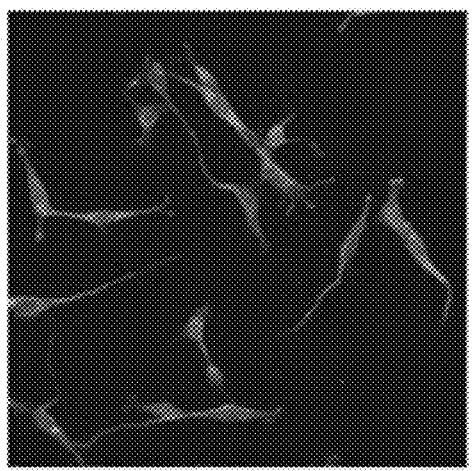
Figure 2B:
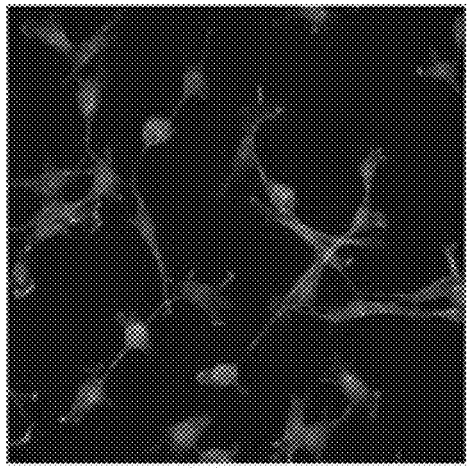

Cytocompatibility Testing:

To assess the potential for use in biomedical applications, the cytocompatibility of ELY$_{16}$ and mELY$_{16}$ was tested. Testing was performed in compliance with ISO 10993-5 standards for in vitro evaluation of cytotoxicity by growing cells for >24 h in direct contact with the material. Using a LIVE/DEAD cytotoxicity kit, the viability of NIH/3T3 fibroblasts cultured for 48 h directly on an adsorbed layer of ELY$_{16}$, mELY$_{16}$, or PLL (positive control) was first measured. Quantified results are shown in FIG. 2A, which shows cytocompatibility of ELY$_{16}$ and mELY$_{16}$. NIH/3T3 fibroblasts were cultured directly on an adsorbed layer of ELY$_{16}$ or mELY$_{16}$ for 48 h, after which they were tested with a LIVE/DEAD assay to assess viability, or as shown in FIG. 2B regarding actin staining to assess morphology. FIG. 2A shows that cell viabilities on ELY$_{16}$ and mELY$_{16}$ are statistically similar to cell viability on the positive control surface, PLL. All groups demonstrate >95% viability. Groups with identical letters are statistically similar (p>0.05) as determined by Tukey's HSD post hoc test. FIG. 2B shows that cells grown on PLL show normal spread morphology. Cells grown on ELY$_{16}$ and mELY$_{16}$ are slightly less spread but still relatively healthy. Scale bar represents 50 μm. In all groups, viability was >95%. Additionally, the viability in both ELP groups was statistically similar to the positive control group. Therefore, neither ELY$_{16}$ nor mELY$_{16}$ has an effect on cellular viability.

To assess the effect of ELY$_{16}$ and mELY$_{16}$ on cellular morphology, actin staining was also performed. As shown in FIG. 2B referenced above, cells grown on PLL display normal spread fibroblast morphology. Cells grown on ELY$_{16}$ or mELY$_{16}$ exhibit less spreading, which is likely due to the observation that cells grown on ELY$_{16}$ and mELY$_{16}$ did not attach as firmly to the surfaces. However, cells on ELY$_{16}$ and mELY$_{16}$ still appear healthy with relatively normal morphology.

Figure 3:
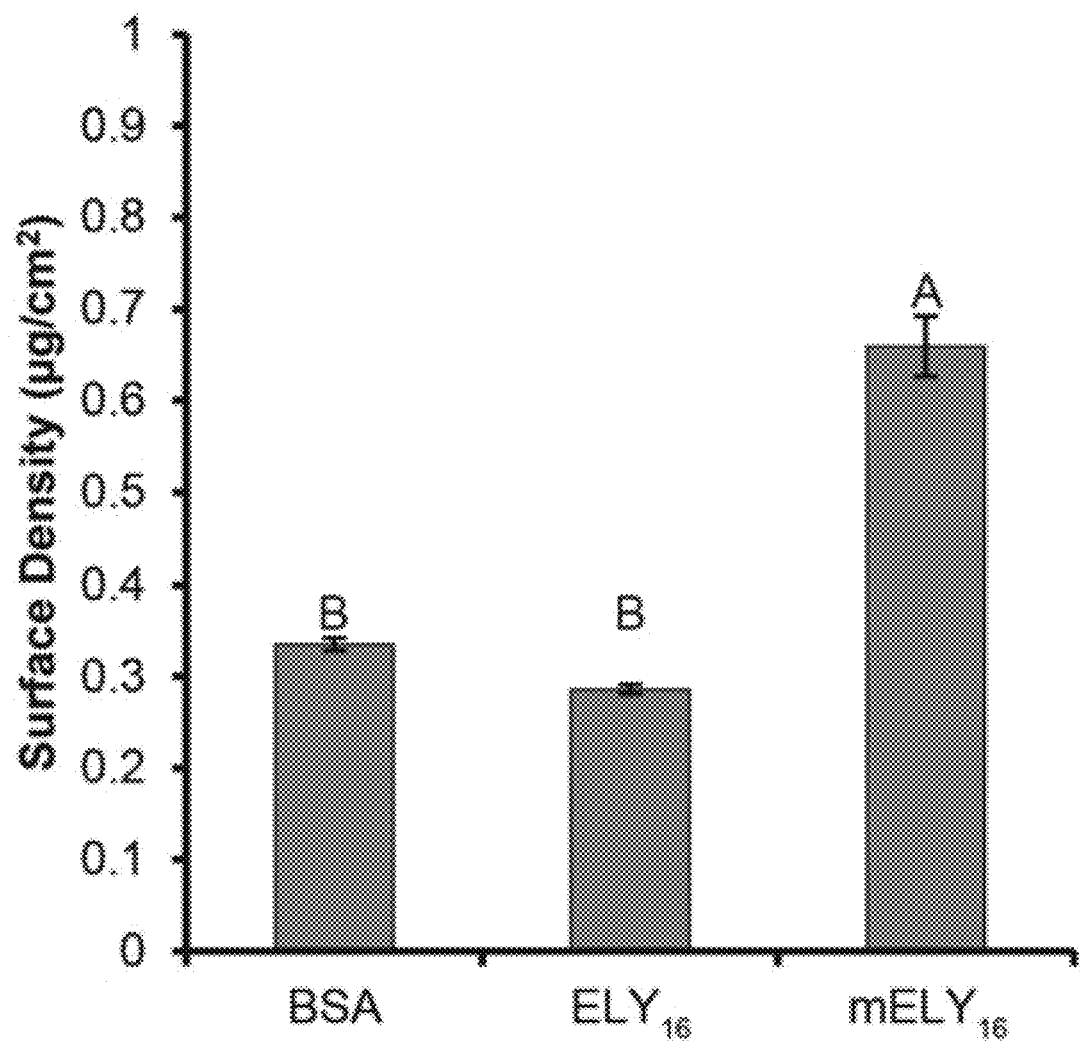
FIG. 3 shows a chart of relative surface densities of BSA, an ELY, and a modified ELY adsorbed to glass, according to an exemplary embodiment of the present disclosure.

Adsorption:

To assess the surface coating abilities of ELY$_{16}$ and mELY$_{16}$, the amount of protein adsorbed to glass coverslips was measured. Additionally, this allowed for quantification of the amount of protein on each surface during cytocompatibility testing. Using BSA as a control protein, protein adsorption was quantified with a BCA assay. FIG. 3 shows that BSA and unmodified ELY$_{16}$ adsorb to glass at similar densities (~0.3 μg/cm$^2$) whereas mELY$_{16}$ adsorbs significantly more strongly at more than twice the surface density (0.66 μg/cm$^2$). The addition of DOPA to ELY$_{16}$ significantly increases its adsorption to glass, as shown in FIG. 3. Protein solutions of BSA (control protein), ELY$_{16}$, and mELY$_{16}$ were adsorbed to acid-washed glass coverslips overnight at 4° C. then washed several times before quantification with a BCA assay. Groups with identical letters are statistically similar (p>0.05) as determined by Tukey's HSD post hoc test.

Lap Shear Adhesion:

Lap shear adhesion testing of ELY$_{16}$ and mELY$_{16}$ was performed in both dry and humid environments to investigate their potential as bulk adhesives, as shown in FIGS. 4A and 4B, which show shear adhesion testing of ELY$_{16}$ and mELY$_{16}$ in a dry environment (FIG. 4A) and in a humid environment (FIG. 4B). In each condition, ELY$_{16}$ and mELY$_{16}$ were compared with BSA as a negative control protein and the fibrin sealant Tisseel as a commercial comparison. As shown in FIG. 4A, and in dry conditions, both ELY$_{16}$ and mELY$_{16}$ exhibited significantly higher adhesion strength than either control group. As shown in FIG. 4B, and in humid conditions, the addition of DOPA to ELY$_{16}$ provided enhanced adhesion strength compared with ELY$_{16}$ alone, BSA, or Tisseel. So to perform the testing in connection with FIG. 4B, the humid (or wet) environments were kept humid by wrapping the various substrates in damp towels, for example, so that the various "glue" products tested were not in direct contact with water. Groups with identical letters are statistically similar (p>0.05) as determined by either the Games-Howell (for dry cure) or Tukey's HSD (for humid cure) post hoc test. BSA was used as a negative control protein, and the fibrin sealant Tisseel was used as a commercial adhesive comparison. After a 24 h dry cure at 37° C., $ELY_{16}$ and $mELY_{16}$ exhibited statistically similar strengths of 2.6 and 2.1 MPa, respectively; these strengths were significantly higher than either BSA (0.1 MPa) or Tisseel (0.7 MPa). When cured in a 100% humid environment, however, the adhesion strength of $mELY_{16}$ (0.24 MPa) was significantly higher than that of $ELY_{16}$ alone (0.05 MPa), BSA (0.07 MPa), or Tisseel (0.07 MPa). These results indicate that addition of DOPA contributed wet adhesive strength to $mELY_{16}$ and that its strength in a humid environment exceeds that of a commercial tissue sealant.

Figure 5A:
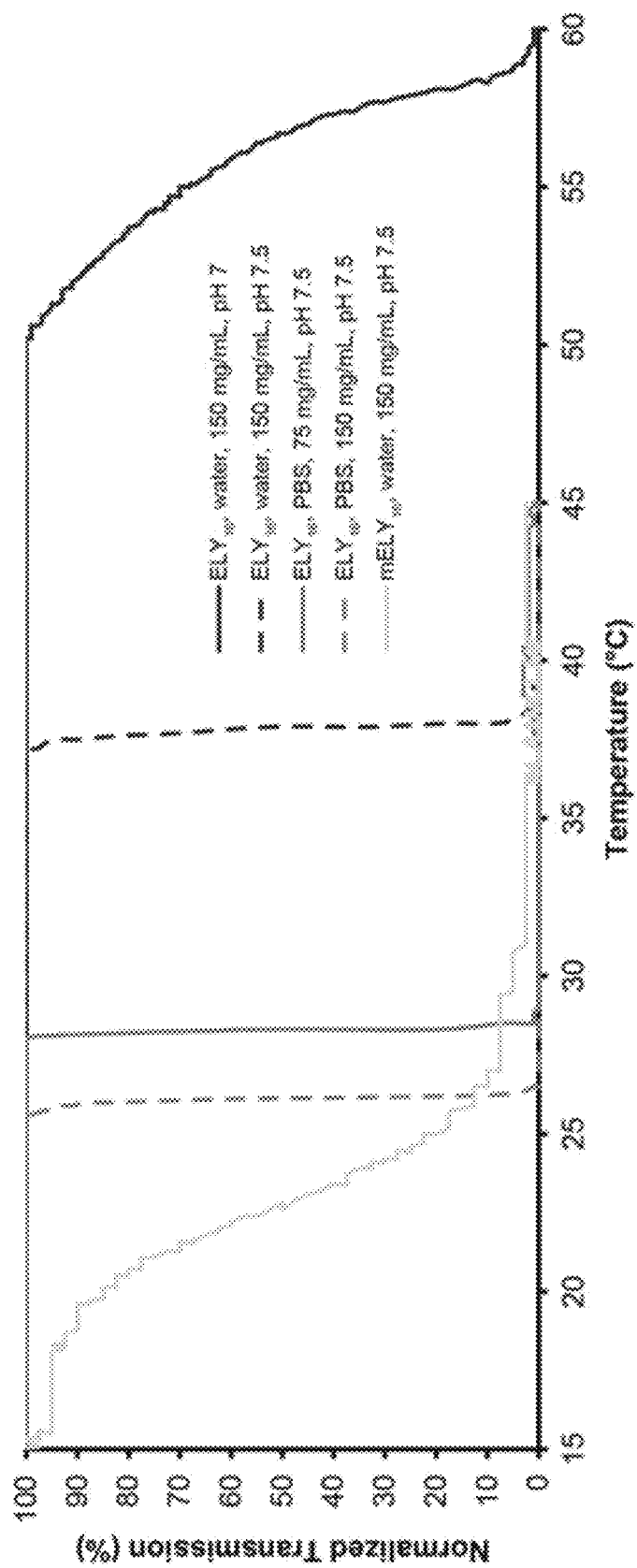
FIG. 5A shows a graph of phase transition behavior of two ELPs within water or buffer at two pH values, according to an exemplary embodiment of the present disclosure.

Coacervation and Underwater Adhesion:

One of the attractive properties of ELPs is their ability to form a phase-separated coacervate at a tunable LCST. To assess their tunability, the LCSTs of both $ELY_{16}$ and $ELY_{16}$ was measured in conditions relevant to adhesion testing and biomedical applications (FIG. 5A). In water at 150 mg/mL, the LCST of $ELY_{16}$ was 38° C. The addition of salt via PBS or higher protein concentrations resulted in lower LCSTs; at 150 mg/mL in PBS, the LCST was lowered to 26° C., whereas at 75 mg/mL in PBS, the LCST was 28° C. Finally, the LCST of $mELY_{16}$ at 150 mg/mL in water was 23° C., a value much lower than that of $ELY_{16}$ alone.

Figure 5B:
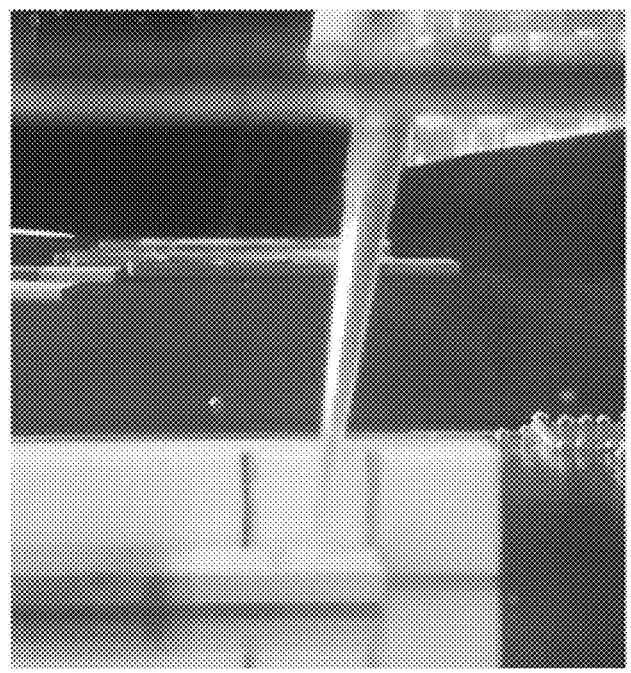
FIG. 5B and FIG. 5C show photographs of coacervation of an ELP introduced underwater, according to exemplary embodiments of the present disclosure.
Figure 5C:
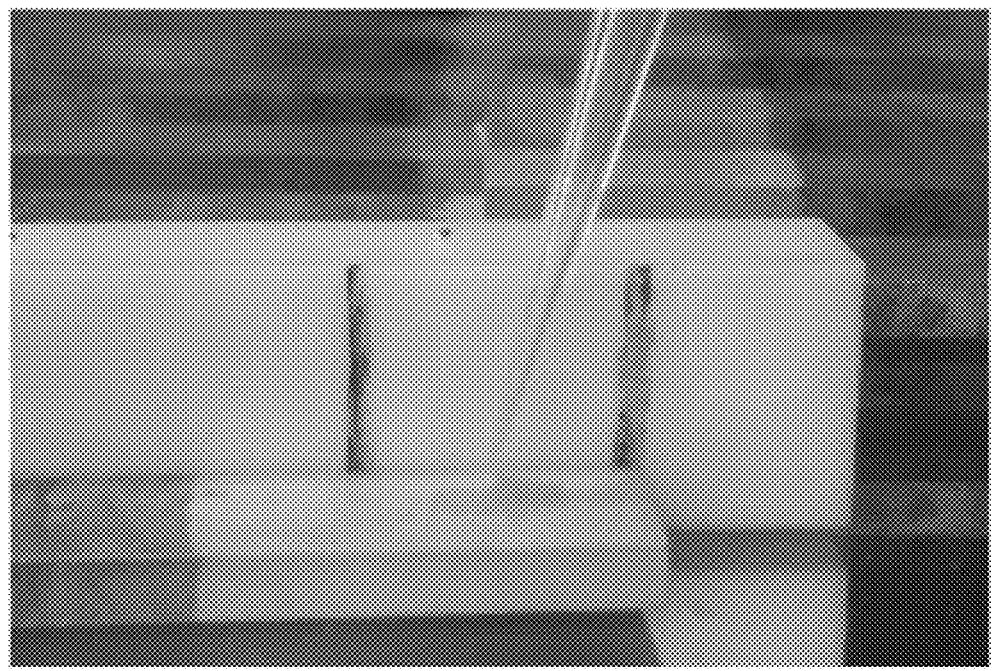

FIGS. 5A, 5B, and 5C show that phase transition behavior of $ELY_{16}$ and $mELY_{16}$ allows for underwater adhesive application. FIG. 5A, as referenced above, shows turbidity testing of $ELY_{16}$ and $mELY_{16}$ at pH 7.5 to determine the tunability of the LCST. The sharp decrease in light transmission corresponds to a rise in turbidity associated with the onset of coacervation. Adding salt or increasing the protein concentration resulted in lower LCST values. $mELY_{16}$ also demonstrated a much lower LCST value compared with $ELY_{16}$ alone. FIGS. 5B and 5C, as referenced below, are snapshots of videos taken of underwater application of $mELY_{16}$ coacervate.

When raised above its LCST, a solution of $ELY_{16}$ forms a separate protein-rich liquid phase, and this ability can be exploited for underwater adhesive application. As a proof of concept for this technique, solutions of $ELY_{16}$ and $mELY_{16}$ were prepared that would be soluble in water at room temperature but would form a coacervate in PBS at 37° C. These solutions were then applied underwater in a PBS bath to test their adhesion strength. Snapshots of underwater application are shown in FIGS. 5B-C. The underwater adhesion strength of BSA could not be tested as it solubilized immediately in solution. Because Tisseel immediately crosslinks when dispensed, it could be applied underwater and tested; however, underwater application of Tisseel was difficult because it adhered to the applicator tip and dispersed slightly in solution. After a 24 h cure underwater in PBS at 37° C., $mELY_{16}$ exhibited an average adhesion strength of 3 kPa, whereas neither $ELY_{16}$ alone nor Tisseel provided any detectable adhesion strength.

As referenced above, an exemplary ELP of the present disclosure has the sequence comprising a variation of SEQ ID No. 2, wherein $X_2$ is V, $X_3$ is K, and each $X_1$ can be tyrosine (Y), dihydroxyphenylalanine (DOPA), and 3,4,5-trihydroxyphenylalanine (TOPA), as previously referenced herein. FIG. 1B shows an ELP having a T7 tag, a His tag, and a cleavage site, resulting in the sequence comprising a variations of SEQ. 5, wherein $X_2$ is V, $X_3$ is K, and each $X_1$ can be tyrosine (Y), dihydroxyphenylalanine (DOPA), and 3,4,5-trihydroxyphenylalanine (TOPA).

Other ELPs are also specifically identified herein, such as the following:

ELP "Y4"—this ELP has the sequence comprising SEQ ID NO. 4 preceded by SEQ ID No. 13, wherein the SEQ ID No. 1 portion of SEQ ID No. 4 is repeated 8 times, each $X_1$ is Y, each $X_2$ is Y, and $X_3$ is E. SEQ ID No. 13 is the same T7 tag as shown in FIG. 1B, HHHHHHH is the same His tag as shown in FIG. 1B, and DDDDK the cleavage site.

ELP "Y2"—this ELP has the sequence comprising SEQ. ID No. 6.

ELP "acY2"—this ELP has the sequence comprising SEQ ID No. 6, where some portion of lysine (K) is acetylated.

ELP "SKY2"—this ELP has the sequence comprising a variation of SEQ ID No. 3, wherein SEQ ID No. 1 is repeated 8 times, each $X_1$ is Y, each $X_2$ is V, and $X_3$ is K.

In view of the foregoing, various ELPs of the present disclosure can have a sequence comprising SEQ ID No. 2, wherein each $X_1$ is selected from the group consisting of tyrosine (Y), dihydroxyphenylalanine (DOPA), and 3,4,5-trihydroxyphenylalanine (TOPA), wherein each $X_2$ is selected from the group consisting of valine (V), Y, DOPA, and TOPA, wherein each $X_3$ is selected from the group consisting of glutamic acid (E) and lysine (K).

These ELPs, and cross-linking of the same (such as by using tris-hydroxymethyl(phosphine) (THP) as a cross-linking agent), are referenced in further detail below. A cross-linking ratio of amine groups:hydroxyl groups is used as a cross-linking reference.

Figure 9:
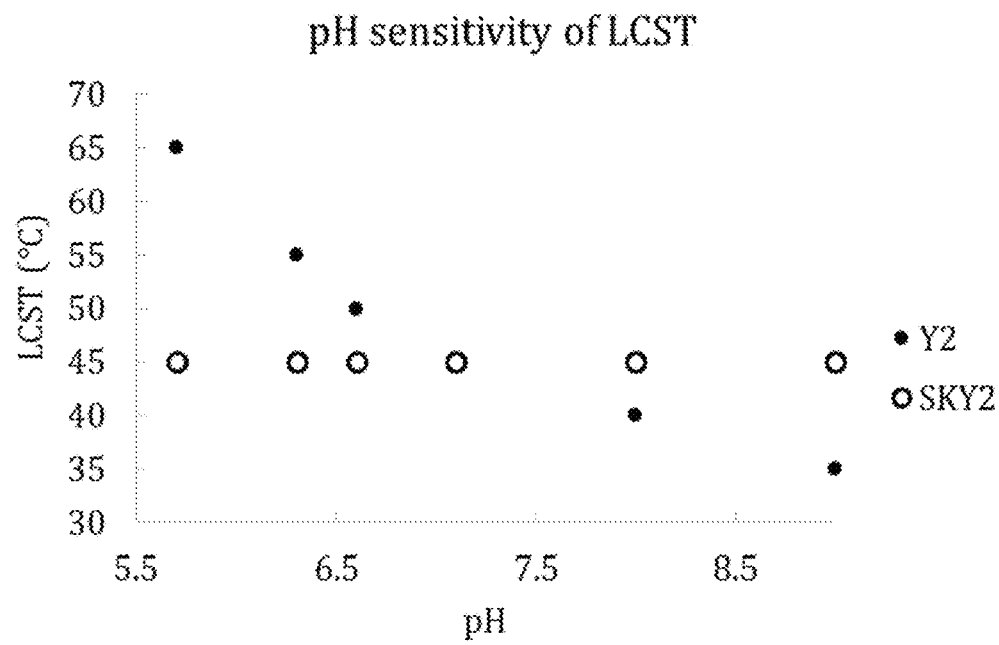
FIG. 9 shows a chart of pH sensitivity of LCST for Y2 and SKY2, according to exemplary embodiments of the present disclosure.

The present disclosure also includes disclosure of data related to the aforementioned ELPs. For example, lower critical solution temperature (LCST) data regarding Y2 and SKY2 is shown in FIG. 9, where Y2 and SKY2 solutions at 10 mg/mL were tested. As shown therein, Y2 has a pH-dependent LCST (lower LCST as pH increases), and SKY2 has no pH-sensitivity in its LCST in the range tested.

Figure 10:
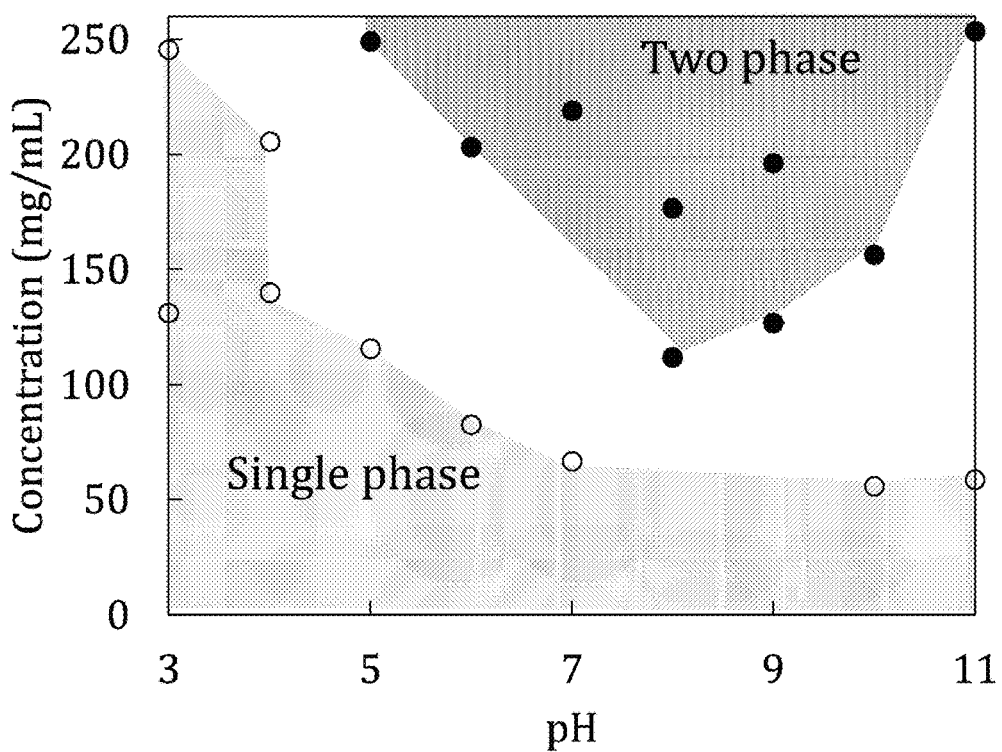
FIG. 10 shows a phase diagram of Y2 and SKY2, according to exemplary embodiments of the present disclosure.

FIG. 10 shows a phase diagram of Y2 in water, showing pH and concentration dependency. LCST behavior causes liquid-liquid phase separation. As shown in FIG. 10, and in Y2, this behavior is pH and concentration dependent. Solutions separate more readily at higher concentrations and at pH between 7 and 9.

Figure 11:
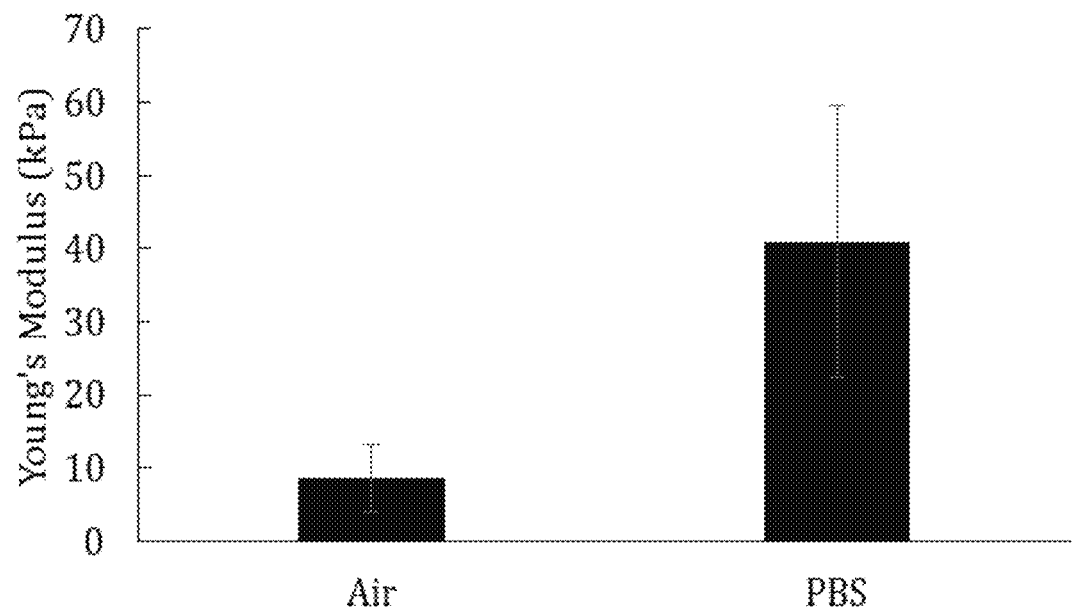
FIG. 11 shows a chart of stiffness of Y4 hydrogels in air and PBS, according to exemplary embodiments of the present disclosure.
Figure 12:
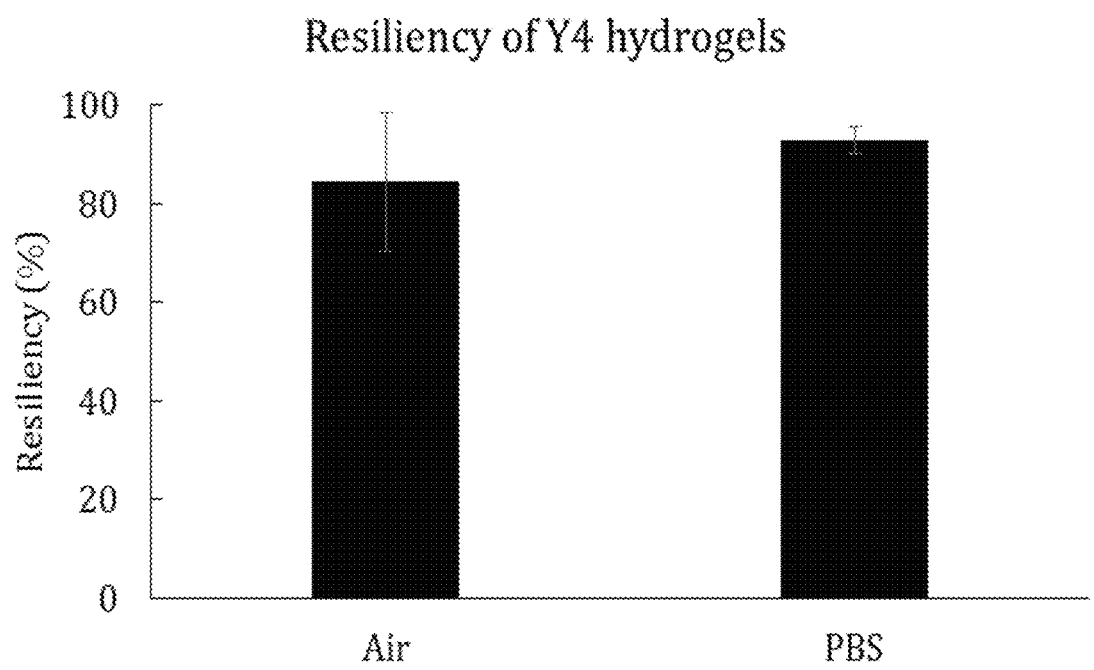
FIG. 12 shows a chart of resiliency of Y4 hydrogels in air and PBS, according to exemplary embodiments of the present disclosure.

Mechanical properties were also tested, such as shown in FIG. 11 with respect to Y4. As shown therein Y4 was tested at 10 w %, 1:24 crosslinking ratio Y4 hydrogels before swelling (air), and after swelling in PBS. Swelling in PBS significantly increases the stiffness of Y4 hydrogels as shown therein. FIG. 12 shows resiliency data, with Y4 tested at 10 w %, 1:24 crosslinking ratio Y4 hydrogels before swelling (air), and after swelling in PBS. Swelling in PBS slightly increases resiliency of Y4 hydrogels.

Figure 13:
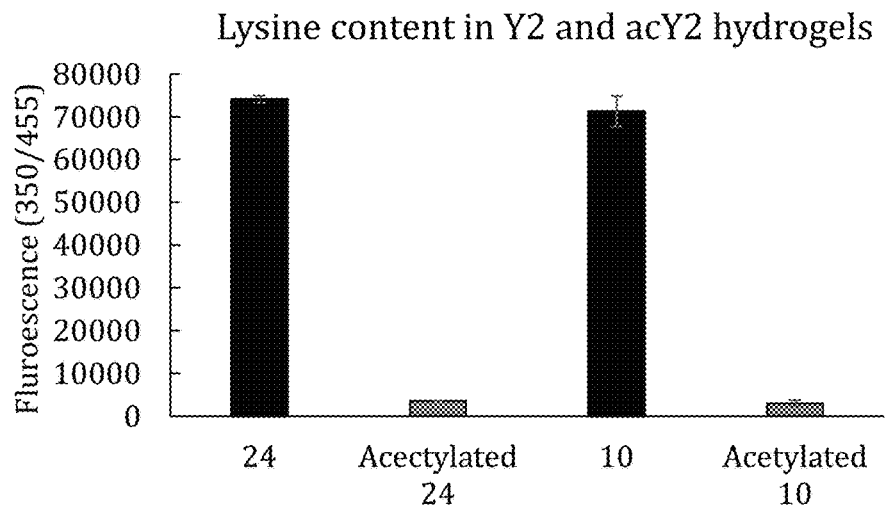
FIG. 13 shows a chart of lysine content in Y2 and acY2 hydrogels, according to exemplary embodiments of the present disclosure.
Figure 14:
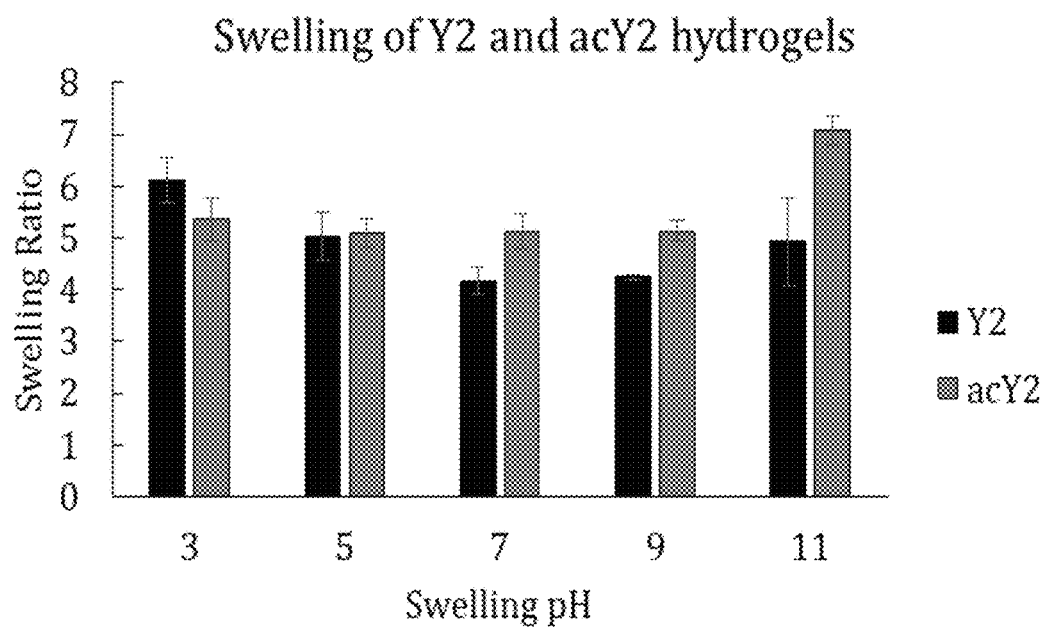
FIG. 14 shows a chart of swelling of Y2 and acY2 hydrogels, according to exemplary embodiments of the present disclosure.

Compressive testing was also performed using Y2 and acY2. FIG. 13 shows a chart of lysine content in Y2 and acY2, Lysine content in hydrogels (made at 14 w % and 1:24 or 1:10 crosslinking ratio with THP) before (Y2) and after acetylation (acY2). Lysine content significantly decreases after acetylation. FIG. 14 shows a chart of swelling of the same two hydrogels (14 w %, and a 1:24 crosslinking ratio), swollen at pH 3-11. Y2 gels have higher swelling ratios at pH further from 7. Acetylating Y2 hydrogels reduces pH sensitivity of swelling.

Figure 15:
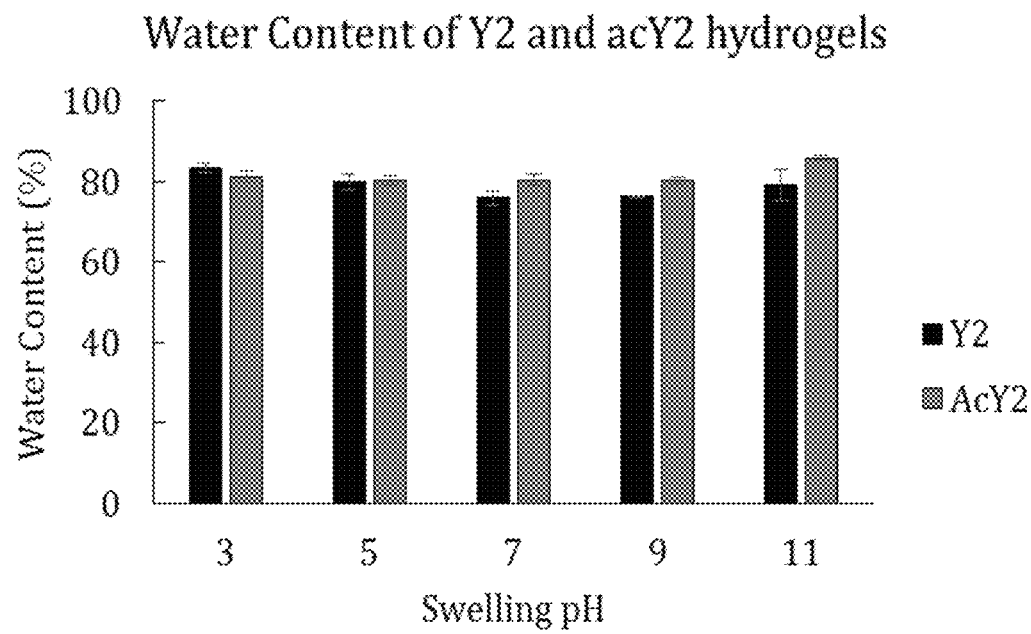
FIG. 15 shows a chart of water content of Y2 and acY2 hydrogels, according to exemplary embodiments of the present disclosure.
Figure 16:
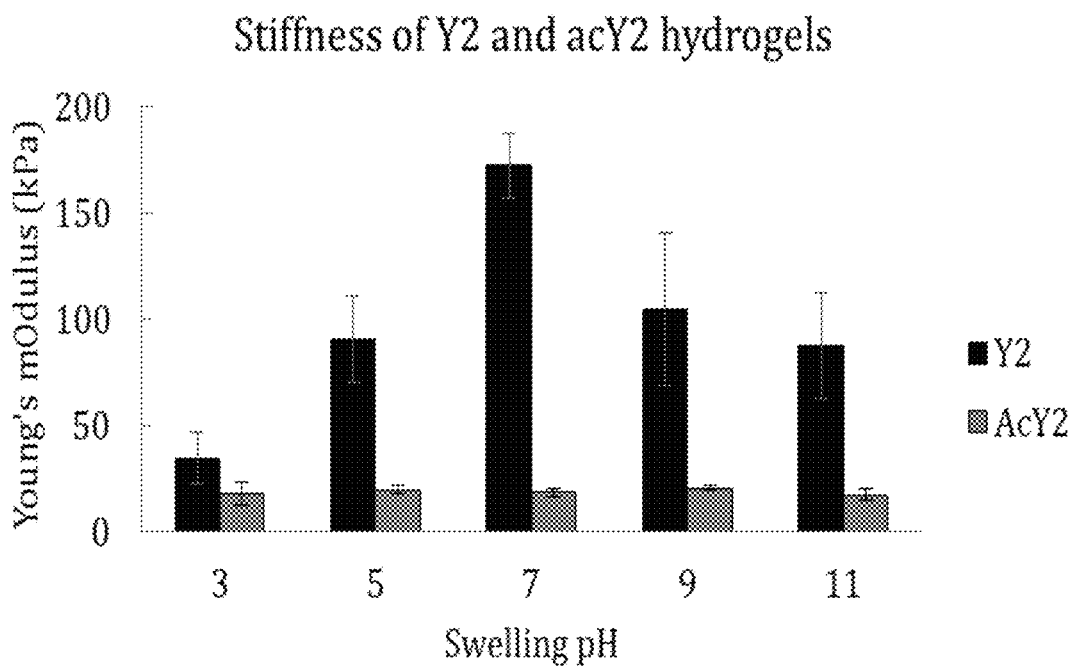
FIG. 16 shows a chart of stiffness of Y2 and acY2 hydrogels, according to exemplary embodiments of the present disclosure.
Figure 17:
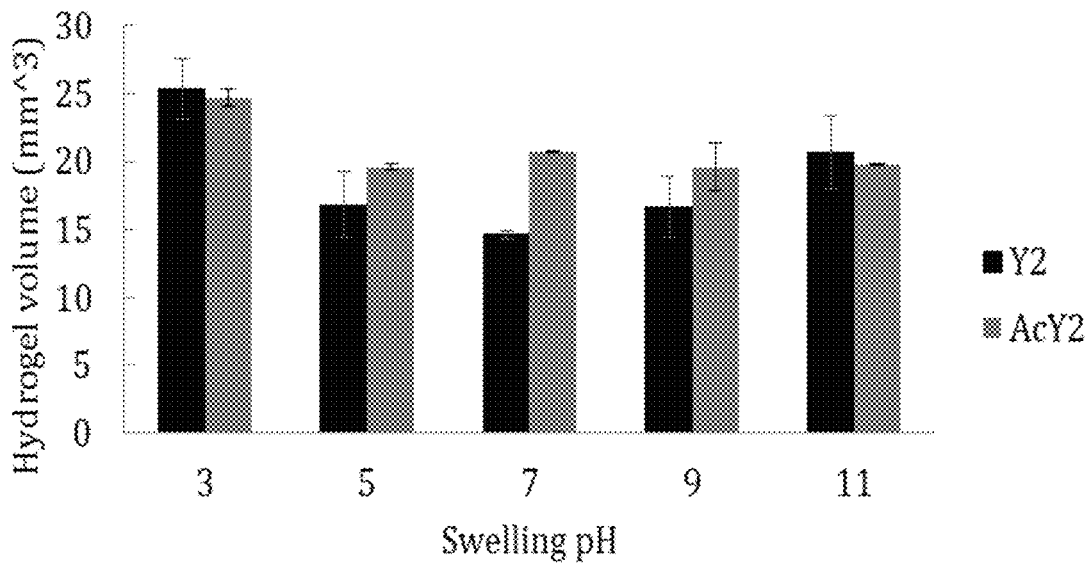
FIG. 17 shows a chart of sizes of Y2 and acY2 hydrogels, according to exemplary embodiments of the present disclosure.

FIG. 15 shows a chart of water content at 14 w % and a 1:24 crosslinking ratio, with the Y2 and acY2 hydrogels swollen at pH 3-11. Water content is between 80-90% for all tested groups. Acetylating Y2 hydrogels does not affect their water content as shown therein. FIG. 16 shows a stiffness chart of the same hydrogels referenced above. Y2 gels are stiffer at pH 7 and softer at pH further from 7. Acetylating Y2 hydrogels removes their pH sensitivity and softens them, as shown therein. The sizes of the two hydrogels (volume) were also tested, as shown in FIG. 17. Y2 hydrogels are smaller when swollen at pH 7. Acetylating Y2 hydrogels reduces this effect.

Figure 18:
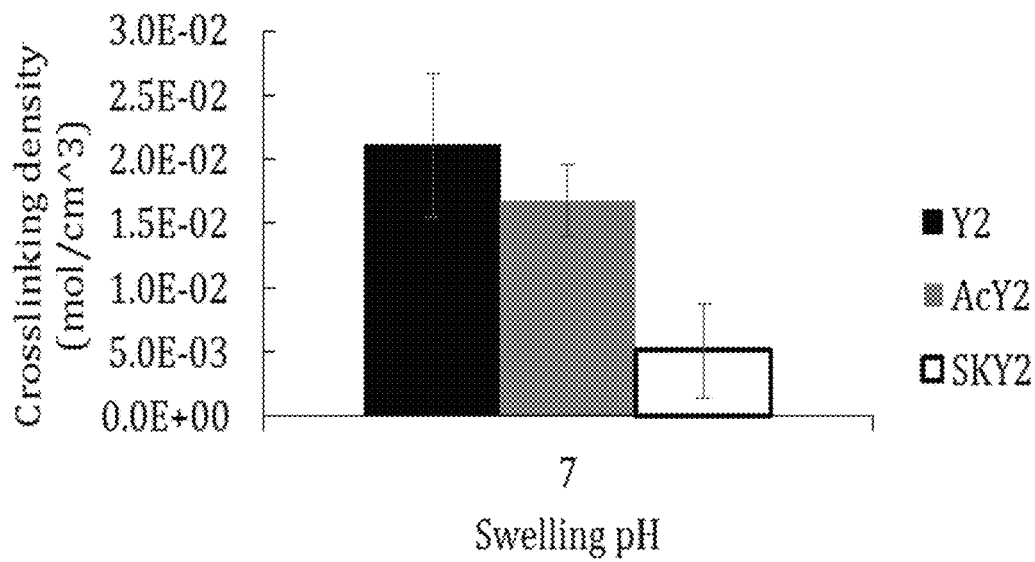
FIG. 18 shows a chart of cross-linking density of Y2, acY2, and SKY2 hydrogels, according to exemplary embodiments of the present disclosure.

FIG. 18 shows crosslinking densities of 14 w %, 1:24 crosslinking ratio Y2, acY2, and SKY2 hydrogels swollen at pH 7. Crosslinking density is a measure of the number of crosslinking junctions per volume. As shown therein, SKY2 hydrogels have a much lower crosslinking density than Y2 hydrogels crosslinked at the same crosslinking ratio.

Figure 19:
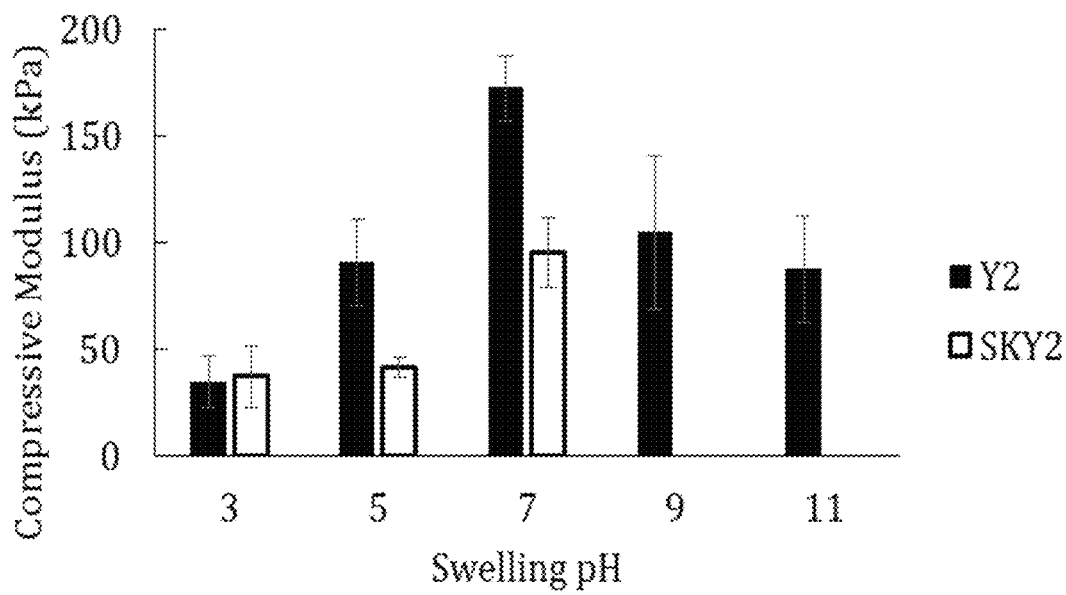
FIG. 19 shows a chart of stiffness of Y2 and SKY2 hydrogels at different pH levels, according to exemplary embodiments of the present disclosure.
Figure 20:
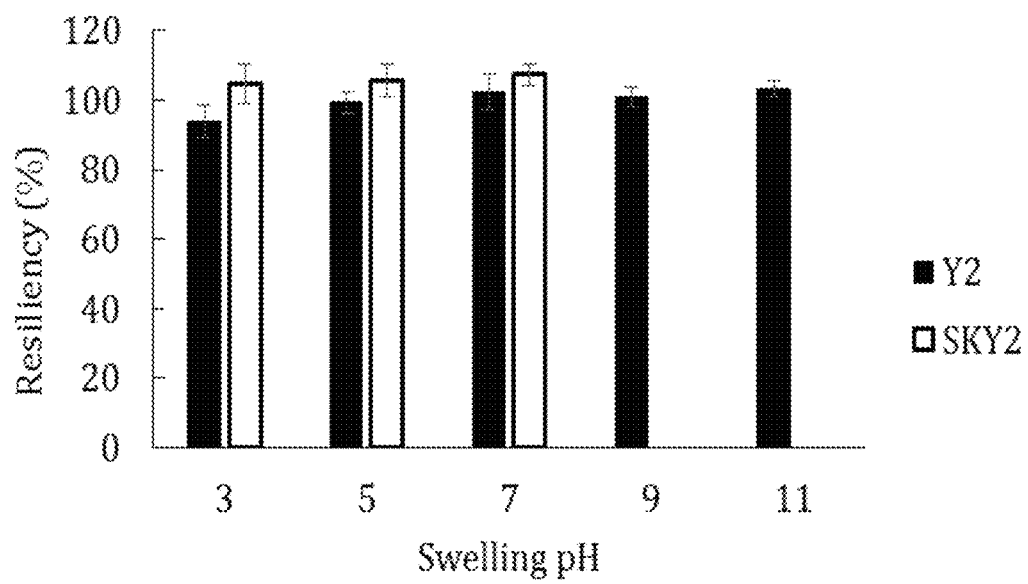
FIG. 20 shows a chart of resiliency of Y2 and SKY2 hydrogels at different pH levels, according to exemplary embodiments of the present disclosure.
Figure 21:
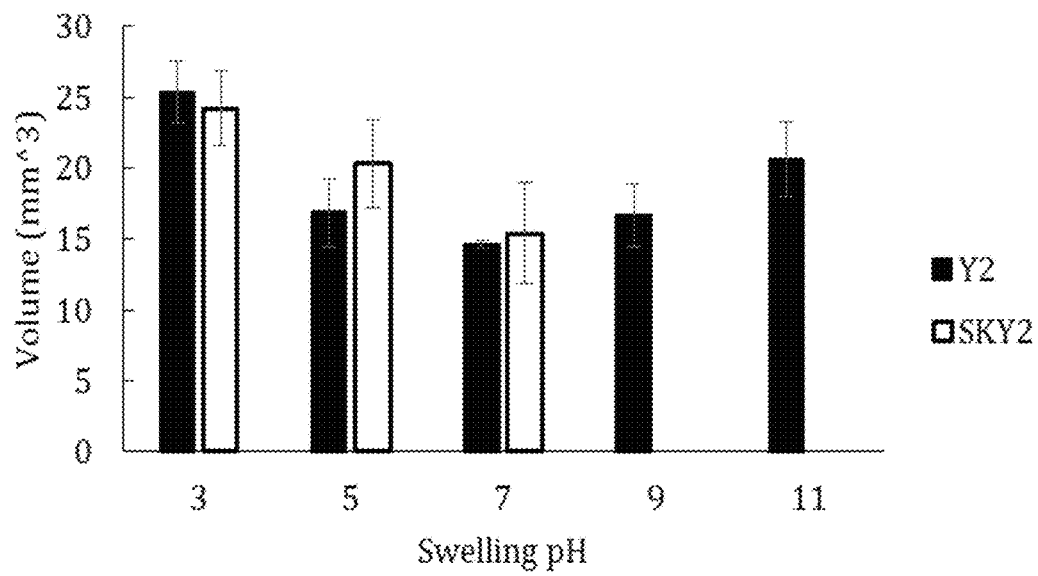
FIG. 21 shows a chart of sizes of Y2 and SKY2 hydrogels at different pH levels, according to exemplary embodiments of the present disclosure.

Additional mechanical properties were also determined. FIG. 19 shows a chart of stiffness data of 14 w %, 1:24 crosslinking ratio Y2 and SKY2 hydrogels swollen at pH 3-11. The stiffness of SKY2 hydrogels has reduced pH sensitivity compared to Y2 hydrogels. Resiliency data was also obtained for the same two hydrogels, as shown in FIG. 20. All gels have high resiliency, above 90%. Resiliency is lowest in Y2 hydrogels at pH 3. FIG. 21 shows size data od the same two hydrogels, whereby SKY2 hydrogels decrease in size near pH 7 as shown therein.

Figure 22:
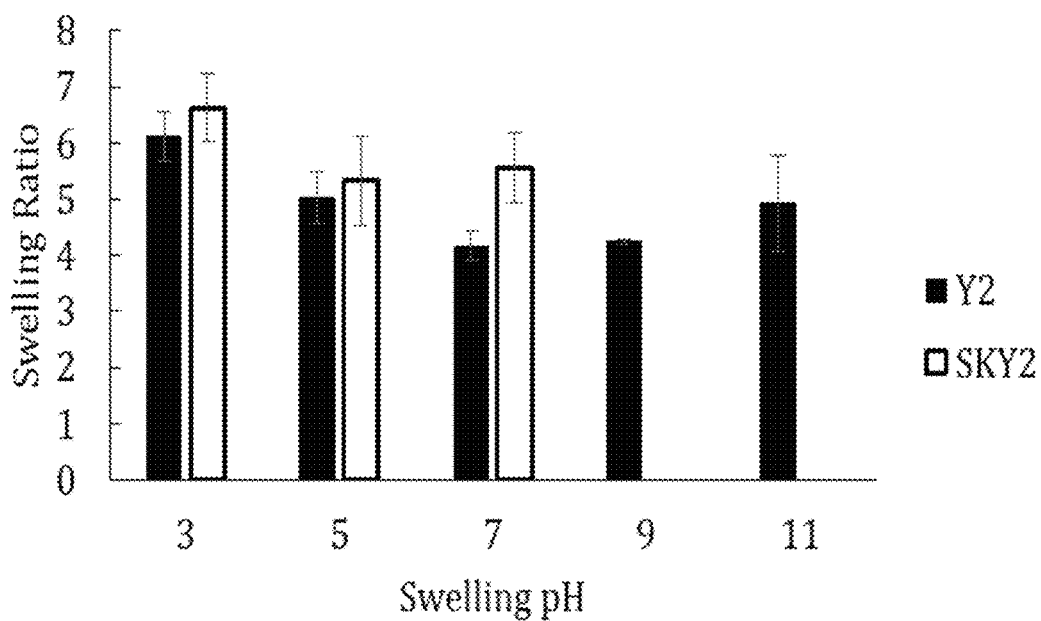
FIG. 22 shows a chart of swelling of Y2 and SKY2 hydrogels at different pH levels, according to exemplary embodiments of the present disclosure.
Figure 23:
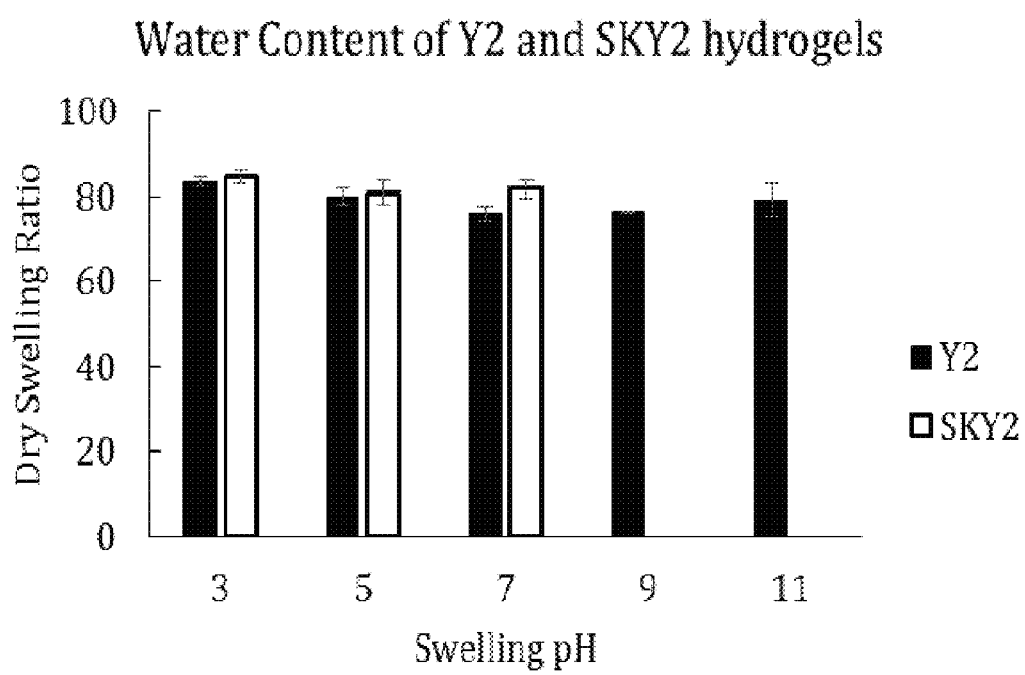
FIG. 23 shows a chart of water content of Y2 and SKY2 hydrogels at different pH levels, according to exemplary embodiments of the present disclosure.

FIG. 22 shows swelling data for the same two hydrogels. SKY2 hydrogels have reduced pH-sensitivity in their swelling ratio, and do not shrink as much near pH 7 as Y2 hydrogels, as identified the figure. Water content (dry swelling ration) data is included in FIG. 23 for the same two hydrogels, whereby the water content of all gels is between 70 and 90%.

In addition to the foregoing, a written Sequence Listing for the above-described artificial sequences is appended hereto and the same Sequence Listing is provided in computer readable form encoded in a file filed on even date with the present disclosure and herein incorporated by reference. The information recorded in computer readable form is identical to the written Sequence Listing provided herein, pursuant to 37 C.F.R. § 1.821(f).

While various embodiments of protein-based adhesives and methods of producing the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An elastin-like polypeptide comprising LDGTL-(PGX$_1$GVPGKGVPGX$_2$GVPGX$_1$GVPGX$_3$GVPGX$_2$GV)$_n$-PVADRGMRLE (SEQ ID NO: 2), wherein:
- each X$_1$ is independently selected from the group consisting of tyrosine (Y), dihydroxyphenylalanine (DOPA), and 3,4,5-trihydroxyphenylalanine (TOPA);
- each X$_2$ is independently selected from the group consisting of valine (V), Y, DOPA, and TOPA,
- X$_3$ is independently selected from the group consisting of glutamic acid (E) and lysine (K), and
- n is an integer from 6 to 10.

2. The elastin-like polypeptide of claim 1, wherein n is 8.

3. The elastin-like polypeptide of claim 1, comprising DDDDK-LDGTL-(PGX$_1$GVPGKGVPGX$_2$GVPGX$_1$GVPGX$_3$GVPGX$_2$GV)$_n$-PVADRGMRLE (SEQ ID NO: 7), wherein:
- each X$_1$ is independently selected from the group consisting of Y, DOPA, and TOPA;
- each X$_2$ is independently selected from the group consisting of V, Y, DOPA, and TOPA;
- X$_3$ is independently selected from the group consisting of E and K;
- n is an integer from 6 to 10; and
- the sequence N-terminal to LDTGTL (SEQ ID NO: 10) in SEQ ID NO: 7 comprises a cleavage site.

4. The elastin-like polypeptide of claim 3, comprising HHHHHHH-DDDDK-LDGTL-(PGX$_1$GVPGKGVPGX$_2$GVPGX$_1$GVPGX$_3$GVPGX$_2$GV)$_n$-PVADRGMRLE (SEQ ID NO: 4), wherein:
- each X$_1$ is independently selected from the group consisting of Y, DOPA, and TOPA;
- each X$_2$ is independently selected from the group consisting of V, Y, DOPA, and TOPA;
- X$_3$ is independently selected from the group consisting of E and K;
- n is an integer from 6 to 10; and
- the repeating histidine residues at the N-terminus of SEQ ID NO: 4 are a His-tag.

5. The elastin-like polypeptide of claim 4, comprising M-MASMTGGQQMG-HHHHHHH-DDDDK-LDGTL-(PGX$_1$GVPGKGVPGX$_2$GVPGX$_1$GVPGX$_3$GVPGX$_2$GV)$_n$-PVADRGMRLE (SEQ ID NO: 6), wherein:
- each X$_1$ is independently selected from the group consisting of Y, DOPA, and TOPA;
- each X$_2$ is independently selected from the group consisting of V, Y, DOPA, and TOPA;
- X$_3$ is independently selected from the group consisting of E and K;
- n is an integer from 6 to 10; and
- the sequence N-terminal to the His-tag in SEQ ID NO: 6 is a T7 tag.

6. The elastin-like polypeptide of claim 1, having a lower critical solution temperature (LCST) at or between 25° C. and 37° C.

7. The elastin-like polypeptide of claim 1, wherein X$_1$ is Y, X$_2$ is V, and X$_3$ is K.

8. The elastin-like polypeptide of claim 1, wherein at least one X$_1$ is DOPA or TOPA.

9. The elastin-like polypeptide of claim 1, wherein n is 8 and X$_1$ is Y.

10. The elastin-like polypeptide of claim 1, capable of adhering to a substrate when applied to said substrate under wet conditions.

11. The elastin-like polypeptide of claim 1, wherein X$_2$ is V and X$_3$ is K.

12. An elastin-like polypeptide comprising MSKG-PGVDGTL-(PGX$_1$GVPGKGVPGX$_2$GVPGX$_1$GVPGX$_3$GVPGX$_2$GV)$_n$-PVADRGMRLE (SEQ ID NO: 3), wherein:
- each X$_1$ is independently selected from the group consisting of Y, DOPA, and TOPA;
- each X$_2$ is independently selected from the group consisting of V, Y, DOPA, and TOPA;
- X$_3$ is independently selected from the group consisting of E and K; and
- n is an integer from 6 to 10.

13. An elastin-like polypeptide comprising VPGXG repeated at least six times within the elastin-like polypeptide (SEQ ID NO: 8), wherein each X is independently selected from the group consisting of E, K, V, Y, DOPA, and TOPA and at least one X is DOPA or TOPA.

14. A method of generating a polypeptide configured for wet adhesion, comprising the steps of:
- providing an initial polypeptide comprising SEQ ID NO: 9; and
- dissolving the initial polypeptide in a buffer comprising a tyrosinase to form a mixture so that least one tyrosine of the initial polypeptide is converted to dihydroxyphenylalanine (DOPA) within the mixture.

15. The method of claim 14, wherein the step of dissolving further comprises converting at least one DOPA to 3,4,5-trihydroxyphenylalanine (TOPA).

16. The method of claim 14, further comprising the step of:
- adding an acid to the mixture after a first period of time has elapsed so to cease further conversion of tyrosine to DOPA.

* * * * *